US006913884B2

(12) United States Patent
Stuelpnagel et al.

(10) Patent No.: US 6,913,884 B2
(45) Date of Patent: Jul. 5, 2005

(54) COMPOSITIONS AND METHODS FOR REPETITIVE USE OF GENOMIC DNA

(75) Inventors: John R. Stuelpnagel, Encinitas, CA (US); Mark S. Chee, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 379 days.

(21) Appl. No.: 09/931,285

(22) Filed: Aug. 16, 2001

(65) Prior Publication Data

US 2003/0036064 A1 Feb. 20, 2003

(51) Int. Cl.[7] .......................... C12Q 1/68; C12P 19/34; C07H 21/02; C07H 21/04; C07H 21/00
(52) U.S. Cl. .................... 435/6; 435/91.1; 435/91.2; 435/91.51; 536/23.1; 536/24.3; 536/24.33; 536/25.3; 536/25.32
(58) Field of Search ............................ 435/6, 91.1, 91.2, 435/183, 287.1, 287.2, 91.51; 436/94, 501; 536/23.1, 24.3, 24.33, 25.3, 25.32

(56) References Cited

U.S. PATENT DOCUMENTS

| 4,200,110 A | 4/1980 | Peterson et al. |
| 4,499,052 A | 2/1985 | Fulwyler |
| 4,682,895 A | 7/1987 | Costello |

(Continued)

FOREIGN PATENT DOCUMENTS

| EP | 0 269 764 A1 | 6/1988 |
| EP | 0 392 546 A2 | 10/1990 |
| EP | 0 478 319 A1 | 4/1992 |
| EP | 0 723 146 A1 | 7/1996 |

(Continued)

OTHER PUBLICATIONS

Khanna et al., multiplex PCR/LDR for detection of K-ras mutations in primary colon tumors. Oncogene, 18, 27–38, 1999.*

Abel et al., "Fiber–Optic Evanescent Wave Biosensor for the Detection of Oligonucleotides," Anal. Chem. 68:2905–2912 (1996).

Anonymous, "Microsphere Selection Guide," Bandg Laboratories, (Fisher, In) Sep. 1998.

Anonymous, "Fluorescent Microspheres," Tech. Note 19, Bang Laboratories, (Fishers, In) Feb. 1997.

Bangs, L.B., "Immunological Applications of Microspheres," The Latex Course, Bangs Laboratories (Carmel, IN) Apr. 1996.

Barnard et al., "A Fibre–Optic Chemical Sensor with Discrete Sensing Sites," Nature, 353:338–340 (Sep. 1991).

Chen et al., "A Microsphere–Based Assay for Multiplexed Single Nucleotide Polymorphism Analysis Using Single Base Chain Extension," Genome Research, 10(4):549–557 (2000).

Czarnik, "Illuminating the SNP Genomic Code," Modern Drug Discovery, 1(2): 49–55 (1998).

(Continued)

Primary Examiner—Kenneth R. Horlick
Assistant Examiner—Frank W Lu
(74) Attorney, Agent, or Firm—McDermott Will & Emery LLP

(57) ABSTRACT

The present invention relates to detection or genotyping (or other sample analysis) of target nucleic acids following immobilization of the target nucleic acids onto a surface. The target nucleic acids can be re-used multiple times, thus conserving sample materials and simplifying sample preparation.

36 Claims, 5 Drawing Sheets

U.S. PATENT DOCUMENTS

| | | |
|---|---|---|
| 4,785,814 A | 11/1988 | Kane |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. |
| 5,435,724 A | 7/1995 | Goodman et al. |
| 5,474,895 A | 12/1995 | Ishii et al. |
| 5,481,629 A | 1/1996 | Tabuchi |
| 5,494,798 A | 2/1996 | Gerdt et al. |
| 5,494,810 A | 2/1996 | Barany et al. |
| 5,496,997 A | 3/1996 | Pope |
| 5,512,490 A | 4/1996 | Walt et al. |
| 5,516,635 A | 5/1996 | Ekins et al. |
| 5,565,324 A | 10/1996 | Still et al. |
| 5,573,909 A | 11/1996 | Singer et al. |
| 5,575,849 A | 11/1996 | Honda et al. |
| 5,633,972 A | 5/1997 | Walt et al. |
| 5,639,603 A | 6/1997 | Dower et al. |
| 5,656,241 A | 8/1997 | Seifert et al. |
| 5,679,524 A | 10/1997 | Nikiforov et al. |
| 5,690,894 A | 11/1997 | Pinkel et al. |
| 5,814,524 A | 9/1998 | Walt |
| 5,830,711 A | 11/1998 | Barany et al. |
| 5,840,256 A | 11/1998 | Demers et al. |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,876,924 A * | 3/1999 | Zhang et al. ................ 435/5 |
| 5,888,723 A | 3/1999 | Sutton et al. |
| 5,900,481 A | 5/1999 | Lough et al. |
| 6,013,456 A | 1/2000 | Akgavan-Tafti |
| 6,023,540 A | 2/2000 | Walt et al. |
| 6,027,889 A | 2/2000 | Barany et al. |
| 6,051,380 A | 4/2000 | Sosnowski et al. |
| 6,054,564 A | 4/2000 | Barany et al. |
| 6,083,763 A | 7/2000 | Balch |
| 6,110,678 A | 8/2000 | Weisburg et al. |
| 6,172,218 B1 | 1/2001 | Brenner |
| 6,225,064 B1 * | 5/2001 | Uematsu et al. ............ 435/6 |
| 6,251,639 B1 | 6/2001 | Kurn |
| 6,268,148 B1 | 7/2001 | Barany et al. |
| 6,355,431 B1 * | 3/2002 | Chee et al. .................. 435/6 |

FOREIGN PATENT DOCUMENTS

| | | |
|---|---|---|
| WO | WO 89/11101 A1 | 11/1989 |
| WO | WO 93/02360 A1 | 2/1993 |
| WO | WO 93/25563 A1 | 12/1993 |
| WO | WO 96/03212 A1 | 2/1996 |
| WO | WO 97/14028 A2 | 4/1997 |
| WO | WO 97/14928 A1 | 4/1997 |
| WO | WO 97/31256 A2 | 8/1997 |
| WO | WO 97/40385 A1 | 10/1997 |
| WO | WO 98/13523 A1 | 4/1998 |
| WO | WO 98/40726 A1 | 9/1998 |
| WO | WO 98/50782 A3 | 11/1998 |
| WO | WO 98/53093 A1 | 11/1998 |
| WO | WO 98/53300 A2 | 11/1998 |
| WO | WO 99/18434 A1 | 4/1999 |
| WO | WO 99/60170 A1 | 11/1999 |
| WO | WO 99/67414 A1 | 12/1999 |
| WO | WO 99/67641 A2 | 12/1999 |
| WO | WO 00/04372 A1 | 1/2000 |
| WO | WO 00/13004 A2 | 3/2000 |
| WO | WO 00/16101 A2 | 3/2000 |
| WO | WO 00/39587 A1 | 7/2000 |
| WO | WO 00/47996 A2 | 8/2000 |
| WO | WO 00/48000 A1 | 9/2000 |
| WO | WO 00/58516 A2 | 10/2000 |
| WO | WO 00/63437 A2 | 10/2000 |
| WO | WO 00/71243 A1 | 11/2000 |
| WO | WO 00/71992 A1 | 11/2000 |
| WO | WO 00/71995 A2 | 11/2000 |
| WO | WO 00/75373 A2 | 12/2000 |

OTHER PUBLICATIONS

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University, Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Ferguson et al., "A Fiber–Optic DNA Biosensor Microarray for the Analysis of Gene Expression," Nature Biotechnology, 14:1681–1684 (1996).

Fuh et al., "Single Fibre Optic Fluorescence pH Probe," Analyst, 112:1159–1163 (1987).

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Healey et al., "Fiberoptic DNA Sensor Array Capable of Detecting Point Mutations," Analytical Biochemistry, 251:270–279 (1977).

Hirschfeld et al., "Laser–Fiber–Optic "Optrode" for Real Time In Vivo Blood Carbon Dioxide Level Monitoring," Journal of Lightwave Technology, LT–5(7):1027–1033 (1987).

Iannone et al., "Multiplexed Single Nucleotide Polymorphism Genotyping by Oligonucleotide Ligation and Flow Cytometry," Cytometry, 39:131–140 (2000).

Michael et al., "Making Sensors out of Disarray: Optical Sensor Microarrays," Proc. SPIE, 3270: 34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro– and Nanostructures Using Optical Imaging Fibers and there Use as Chemical Sensors," Proc. 3rd Intl. Symp., Microstructures and Microfabricated Systems, ed. P.J. Hesketh, et al., v. 97–5, Electrochem. Soc., 152–157 (Aug. 1997).

Mignani, et al., "In–vivo Biomedical Monitoring by Fiber–Optic Systems," Journal of Lightwave Technology, 13(7): 1396–1406 (1995).

Pantano et al., "Ordered Nanowell Arrays," Chem. Mater., 8(12): 2832–2835 (1996).

Peterson et al., "Fiber–Optic Sensors for Biomedical Applications," Science, 13:123–127 (1984).

Peterson, J. et al., "Fiber Optic pH Probe for Physiological Use," Anal. Chem., 52:864–869 (1980).

Piunno et al., "Fiber–Optic DNA Sensor for Fluorometric Nucleic Acid Determination," Anal. Chem., 67:2635–2643 (1995).

Pope, E. "Fiber Optic Chemical Microsensors Employing Optically Active Silica Microspehres," SPIE, 2388:245–256 (1995).

Strachan et al., "A Rapid General Method for the Identification of PCR Products Using a Fibre–Optic Biosensor and its Application to the Detection of Listeria," Letters in Applied Microbiology, 21:5–9 (1995).

Walt, D. "Fiber Optic Imaging Sensors," Accounts of Chemical Research, 31(5): 267–278 (1998).

Walt, "Fiber–Optic Sensors for Continuous Clinical Monitoring," Proc. IEEE, 80(6): 903–11 (1992).

Lyamichev et al., "Polymorphism identification and quantitative detection of genomic DNA by invasive cleavage of oligonucleotide probes," Nature Biotechnolgoy, 17:292–296 (1999).

Shoemaker et al., "Quantitative phenotypic analysis of yeast deletion mutants using a highly parallel molecular bar–coding strategy," Nature Genetics, 14:450–456 (1996). (A, AS, NA) added Aug. 1, 2001.

* cited by examiner

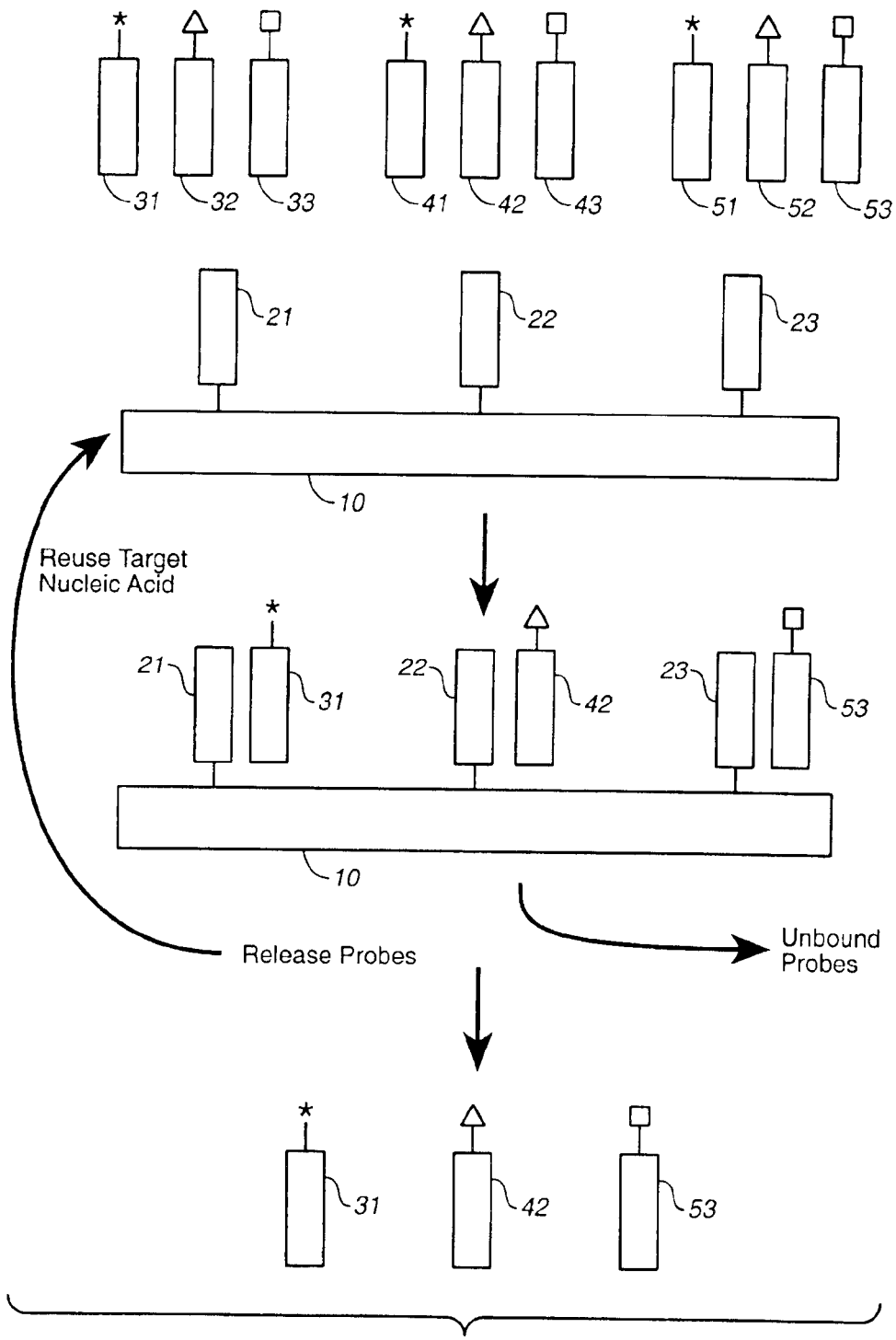
FIG._1

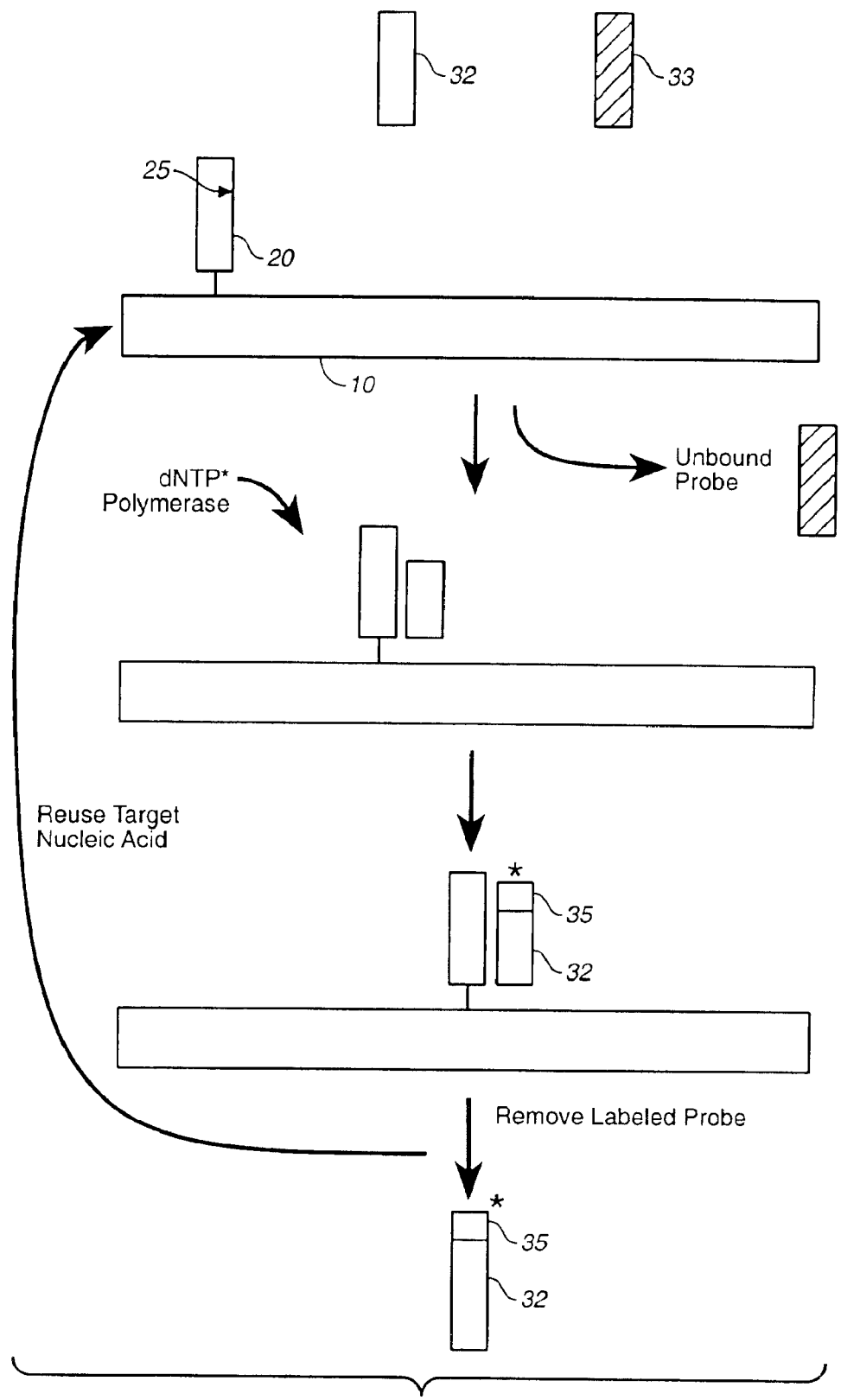
FIG._2

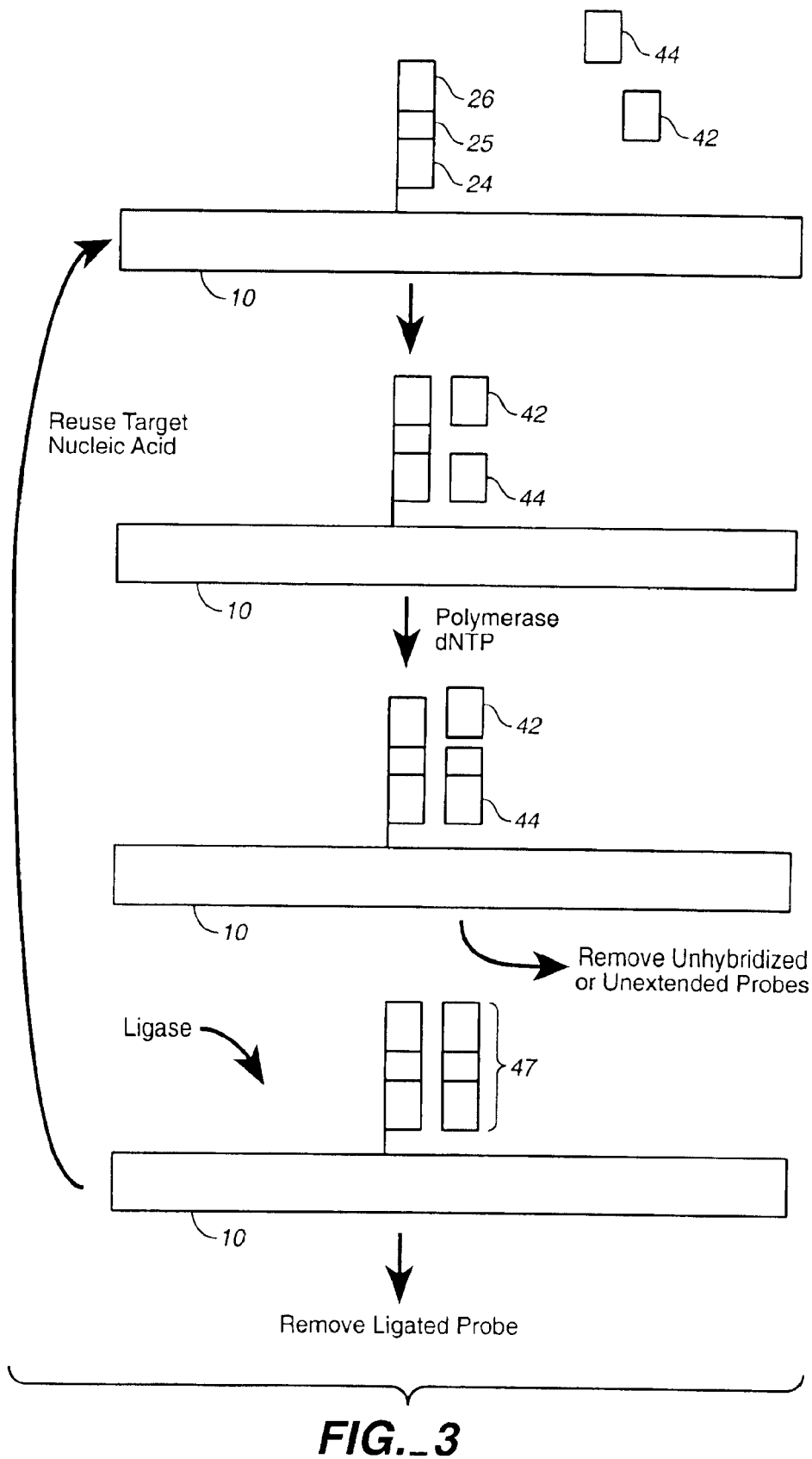
FIG._3

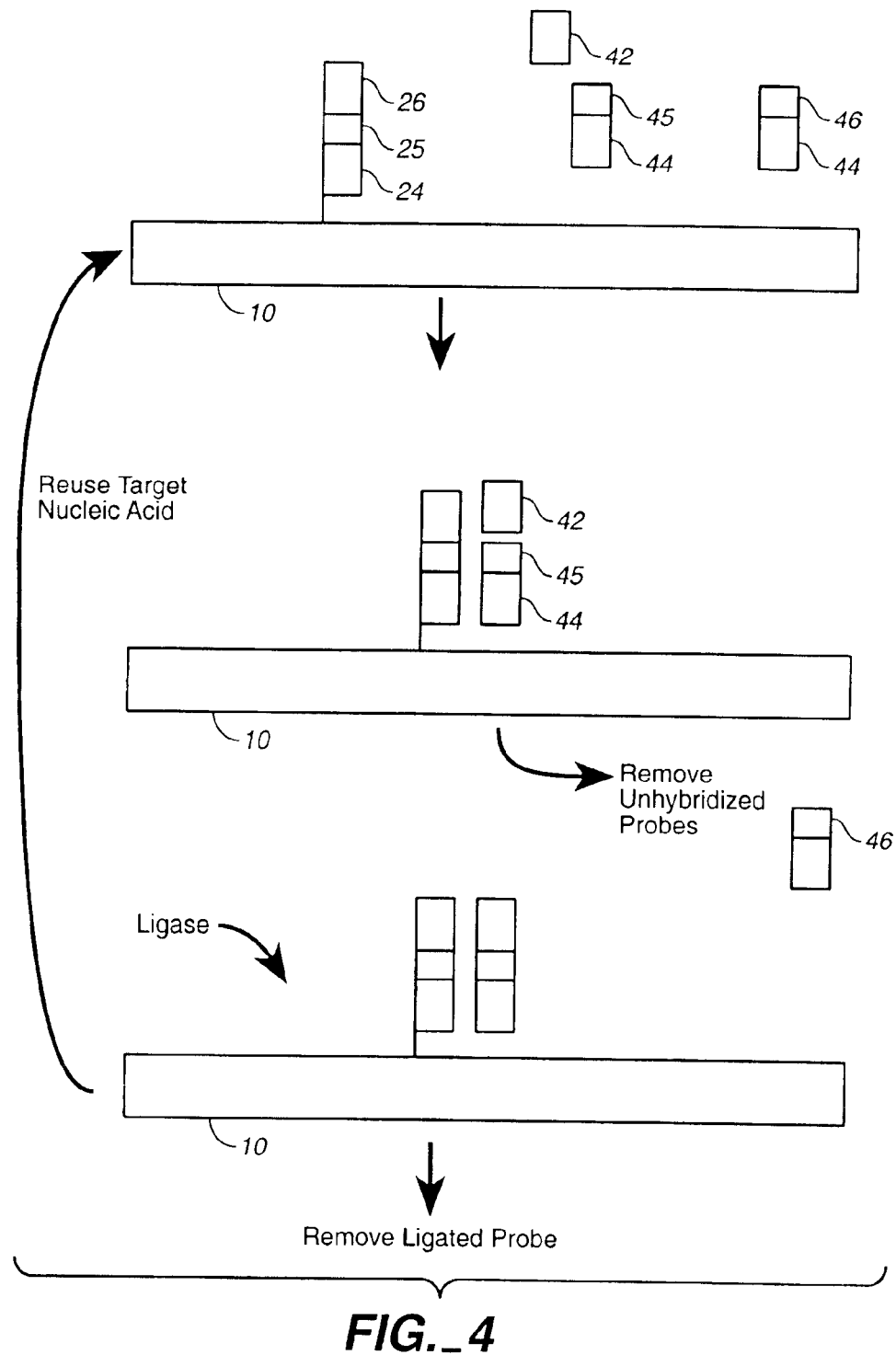
FIG._4

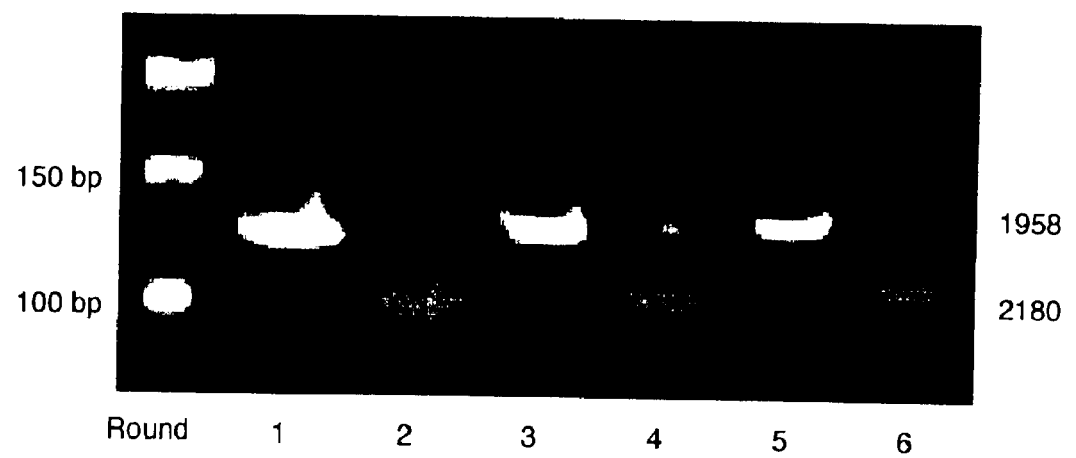
FIG._5
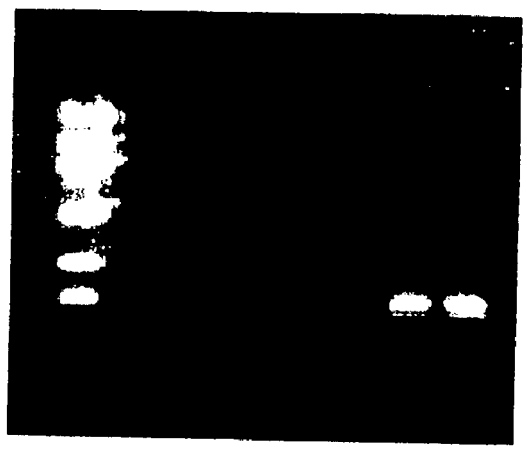
FIG._6A
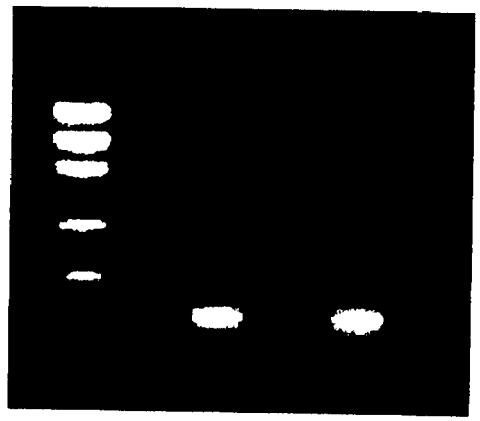
FIG._6B

COMPOSITIONS AND METHODS FOR REPETITIVE USE OF GENOMIC DNA

FIELD OF THE INVENTION

The present invention relates to detection or genotyping (or other sample analysis) of target nucleic acids following immobilization of the target nucleic acids onto a surface. The target nucleic acids can be re-used multiple times, thus conserving sample materials and simplifying sample preparation.

BACKGROUND OF THE INVENTION

The detection of specific nucleic acids is an important tool for diagnostic medicine, molecular biology research and forensic analysis. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261:921–923 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998).

However, difficulty has been encountered in obtaining significant data in large-scale genotyping or SNP identification studies because the target or sample is consumed during the assay. Accordingly, there exists a need for a method of reusing target nucleic acids, in particular, target genomic DNA.

There are a variety of particular techniques that are used to detect sequence, including mutations and SNPs. These include, but are not limited to, ligation based assays, single base extension methods (see WO 92/15712, EP 0 371 437 B1, EP 0317 074 B1; Pastinen et al., Genome Res. 7:606–614 (1997); Syvänen, Clinica Chimica Acta 226:225–236 (1994); and WO 91/13075), cleavage based assays such as Invader™ technology, Q-Beta replicase (QβR) technology and competitive probe analysis (e.g. competitive sequencing by hybridization; see below).

Oligonucleotide ligation amplification ("OLA", which is referred as the ligation chain reaction (LCR) when two-stranded reactions) involves the ligation of two smaller probes into a single long probe, using the target sequence as the template. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256 and WO 89/09835, all of which are incorporated by reference.

An additional technique utilizes sequencing by hybridization. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

PCTs US98/21193, PCT US99/14387 and PCT US98/05025; WO98/50782; and U.S. Ser. Nos. 09/287,573, 09/151,877, 09/256,943, 09/316,154, No. 60/119,323, Ser. No. 09/315,584; all of which are expressly incorporated by reference, describe novel compositions utilizing substrates with microsphere arrays, which allow for novel detection methods of nucleic acid hybridization.

Samples can be scarce and difficult to obtain. Reusing target DNA can be critical in large studies such as SNP genotyping studies, to reduce DNA consumption and sample preparation costs. None of the current methods allow the rapid, facile, repeated and inexpensive analysis of a target nucleic acid by re-using the target after it is immobilized on a substrate. Accordingly, it is an object of the present invention to provide methods and compositions for such determinations.

SUMMARY OF THE INVENTION

In accordance with the objects outlined above, the present invention provides composition comprising a substrate comprising immobilized target nucleic acids. The target nucleic acids comprise genomic DNA and an attachment moiety for attaching the genomic DNA to the substrate, wherein the attachment moiety is capable of withstanding multiple analyses of the genomic DNA.

In addition the invention provides a method comprising providing a substrate comprising a plurality of immobilized genomic DNA target sequences, performing a first analysis of the target sequences whereby the immobilized genomic DNA is not consumed and performing a second analysis of the immobilized genomic DNA target sequences. In a preferred embodiment the first and second analyses are genotyping analyses and can also include amplification reactions.

In addition the invention provides a method comprising providing a substrate comprising a plurality of immobilized genomic DNA sequences, hybridizing the genomic DNA sequences with a first set of ligation primers to form first ligation complexes, whereby the first ligation primers hybridize to the genomic DNA sequences flanking a first target sequence. The method further includes removing unhybridized ligation primers. In addition the method includes contacting the first ligation complexes with a ligation enzyme, whereby when the first ligation primers are complementary to the first target sequences, the ligation enzyme ligates the first ligation primers generating first ligation products. In addition the method includes removing the first ligation products from said immobilized genomic DNA. The invention further includes hybridizing the genomic DNA with second ligation primers to form second ligation complexes, whereby the second ligation primers hybridize to the genomic DNA sequences flanking a second target sequence, contacting the second ligation complex with a ligation enzyme, whereby when the second ligation primers are complementary to the second target sequence, the ligation enzyme ligates said second ligation primers generating second ligation products. The method also includes detection the ligation products.

In addition the invention provides a method comprising providing a composition comprising first primers and target nucleic acid and performing a first analysis of the target nucleic acid wherein the first analysis includes contacting the first primers with the target nucleic acid whereby at least one of the first primers hybridizes with the target nucleic acid. Further the method includes removing unhybridized first primers and contacting the hybridized first primers with an enzyme such that the hybridized first primers are modified forming first modified primers, whereby the target nucleic acid is not consumed, and performing a second analysis of the target nucleic acid.

In addition the invention includes amplifying the products of the genotyping reaction, i.e. the ligation reaction and detecting the amplicons. Detection is accomplished by a variety of methods including mass spectrometry, flow cytometry, ordered arrays, random arrays, capillary electrophoresis and the like.

BRIEF DESCRIPTION OF THE DRAWINGS

FIG. 1 depicts competitive hybridization of target probes (31, 32, 33, 41, 42, 43, 51, 52 and 53) to target sequences (21, 22, and 23) immobilized on a surface 10. The target probes comprise labels (star, triangle and square). Following hybridization, unbound probes are removed from the sample; bound probes are subsequently released and detected. Thus, the samples of target material can be reused.

FIG. 2 depicts single base extension (SBE) assay to detect the base at a detection position 25 in a target nucleic acid 20 that is immobilized to a solid support 10. A set of target probes 32, 33 are contacted with the immobilized target. The unbound probes are removed. Labeled nucleotides and polymerase are added to the complex. A labeled nucleotide 35 that is complementary to the nucleotide at the detection position is incorporated into the target probe 32. The hybridized labeled probe is removed. Now the sample of target nucleic acids can be reused.

FIG. 3 depicts SBE followed by oligonucleotide ligation assay (OLA). Two probes, an upstream 44 and downstream 42 probe are hybridized with target nucleic acid immobilized on a surface 10. The target nucleic acid includes an upstream target sequence 24, a detection position 25 and a downstream target sequence 26. Following hybridization of the probes 42 and 44 to the target nucleic acid, a polymerase and nucleotides that can be optionally labeled are contacted with the hybridization complex. A nucleotide that is complementary to the nucleotide at the detection position is incorporated into the upstream probe 44. Non-extended probes are removed. A ligase is contacted with the hybridization complex and ligates the modified (extended) upstream probe 44 with the downstream probe 42 to form a modified target probe 47. The modified target probe is removed from the immobilized target nucleic acid and the immobilized target nucleic acid is re-used.

FIG. 4 depicts the oligonucleotide ligation assay (OLA). Upstream and downstream ligation probes 42 and 44 are hybridized to target nucleic acids immobilized to a solid support. The target nucleic acid comprises upstream and downstream target sequences 24 and 26, respectively, and a detection position 25. The upstream ligation probes comprise a nucleotide that is complementary to the nucleotide at the detection position 45. The set of upstream ligation probes includes nucleotides that are complementary 45 and those that are not 46. Following hybridization of the probes to the target nucleic acid, the probes that are not complementary at the detection position are removed. Ligase is added. The ligated probes are removed from the immobilized target nucleic acid and detected by various methods including flow cytometry, ordered or positioned arrays, capillary electrophoresis or mass spectrometry. The immobilized target nucleic acid is then re-used.

FIG. 5 demonstrates that solid phase genomic DNA is reusable.

FIG. 6 demonstrates that genomic DNA on magnetic particles is reusable in the oligonucleotide ligation assay. A. OLA assay with 48 Loci. There are two negative controls, (A and B) and two positive controls, (C and D). B. OLA assay with 48 Loci. The same 'beaded' DNA is used the next day. There are two negative controls, (A and C) and two positive controls, (B and D).

DETAILED DESCRIPTION OF THE INVENTION

The present invention is directed to methods of amplification and genotyping, and in particular to methods that include the re-use of genomic DNA in genotyping and amplification assays. The invention can be used with adapter sequences that include universal primers. Products of genotyping reactions are detected by a variety of methods including flow cytometry, positioned arrays, capillary electrophoresis, mass spectrometry or bead arrays as described herein.

The invention can generally be described as follows. A plurality of probes (sometimes referred to herein as "target probes") are contacted with sample genomic DNA that is at some point immobilized to a solid support. That is, the sample can be immobilized either prior to or after hybridization with the probes. Preferably the target probes are designed to have a first portion that is target-specific and two "priming" portions, an upstream and downstream priming sequence, that flank the target specific portion. These priming sequences are preferably "universal"; that is, all target probes have the same priming sequences. These target probes are hybridized to target sequences to form hybridization complexes. Non-hybridized sequences are then removed. This is generally performed by removing the liquid phase containing the non-hybridized probes and optionally washing the immobilized hybridization complexes. Following this step, the sample genomic DNA can be reused. That is, the genomic DNA is not consumed in the analysis or genotyping reaction. By "consumed" is meant degraded or otherwise modified so as to prevent subsequent analysis.

For direct detection of genomic sequences, the hybridization complexes are denatured, and the target probes collected. Then PCR primers (although as described herein, other amplification reactions can be performed) that correspond to the priming sequences are added, and amplification proceeds. Other amplification schemes include but are not limited to T7 amplification and Invader™ technology. The resulting amplicons, which can be directly or indirectly labeled, can then be detected. Detection is accomplished by a variety of methods including flow cytometry, positioned arrays, capillary electrophoresis, mass spectrometry or bead arrays as described herein on arrays. This allows the detection and quantification of the target sequences.

In a preferred embodiment, rather than simple detection, genotyping reactions are performed on the immobilized genomic DNA. A variety of known genotyping reactions can be performed, including, but not limited to oligo ligation assay (OLA), single-base extension (SBE), allelic PCR (aPCR), and cleavage reactions such as Invader™, and the like. In each case, the target probe(s) used for the genotyping reaction contain priming sequences. Preferably, the unhybridized probes are removed prior to the genotyping reaction. Once the genotyping reaction is complete and unhybridized probes have been removed, the hybridization complexes are denatured, and the target probes are amplified. The resulting amplicons are then detected as outlined herein.

One particular strength of the present invention is that the immobilized genomic DNA can be reused indefinitely. The method finds a notable advantage in the ability to generate multiple genotyping or amplification assay products from a single sample of genomic DNA. That is, by reusing genomic DNA, multiple genotypes or amplification reactions can be performed on a single sample. Thus, for example, a first set of target probes directed to a first set of SNPs can be added, reacted and removed, and then a second set of target probes added to a second set of SNPs. This process can be repeated, thus allowing diverse and robust genomic information to be obtained.

As will be appreciated by those in the art, the system can take on a wide variety of conformations, depending on the assay. For example, the oligonucleotide ligation assay (OLA) can be performed. OLA relies on the fact that two adjacently hybridized probes will be ligated together by a ligase only if there is perfect complementarity at each of the termini, i.e. at a detection position. In this embodiment, there are two ligation probes: a first or upstream ligation probe that comprises the upstream priming sequence and a second portion that will hybridize to a first domain of the target sequence, and a second or downstream ligation probe that comprises a portion that will hybridize to a second domain of the target sequence, adjacent to the first domain, and a second portion comprising the downstream priming sequence. If perfect complementarity at the junction exists, the ligation occurs and then the resulting hybridization complex (comprising the target and the ligated probe) can be separated as above from unreacted probes. Again, the priming sites are used to amplify the ligated probe to form a plurality of amplicons that are then detected in a variety of ways, as outlined herein. Alternatively, a variation on this theme utilizes rolling circle amplification (RCA), which requires a single probe whose ends are ligated, followed by amplification.

In addition, any of the above embodiments can utilize one or more "adapter sequences" (sometimes referred to in the art as "zip codes") to allow the use of "universal arrays". That is, arrays are used that contain capture probes that are not target specific, but rather specific to individual artificial adapter sequences. The adapter sequences are added to the target probes (in the case of ligation probes, either probe may contain the adapter sequence), nested between the priming sequences, and thus are included in the amplicons. The adapters are then hybridized to the capture probes on the array, and detection proceeds.

Accordingly, the present invention may include any appropriate methods of amplification and detection of target sequences in a sample. Preferably the target sequence is genomic DNA. In addition the method is directed to re-using target sequences in sequential amplification reactions or other genotyping analyses or assays.

In a preferred embodiment, the present invention provides methods and compositions for the repeated use and detection of target sequences in samples. As will be appreciated by those in the art, the sample solution may comprise any number of things, including, but not limited to, forensic samples, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in U.S. Ser. No. 60/161,148; hereby incorporated by reference) such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The present invention is directed to the repeated detection of target sequences from a sample. By "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. Preferably the target sequence is genomic DNA.

As is outlined herein, the target sequence may be a target sequence from a sample that has been amplified. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, readout probes are made to hybridize to target sequences to determine the presence or absence of the target sequence in a sample. Generally speaking, this term will be understood by those skilled in the art. Preferably, however, the target sequence is not amplified prior to attachment to the solid support.

The target sequence may also be comprised of different target domains. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

By "nucleic acid" or "oligonucleotide" or grammatical equivalents herein means at least two nucleotides covalently linked together. A nucleic acid of the present invention will generally contain phosphodiester bonds, although in some cases, as outlined below (for example for target probes, etc), nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321(1989), O-methyiphophoroamidite linkages (see Eckstein, *Oligonucleotides and Analogues: A Practical Approach,* Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlson et al., *Nature* 380:207 (1996), all of which are incorporated by reference). Other analog nucleic acids include those with positive backbones (Denpcy et al., *Proc. Natl. Acad Sci. USA* 92:6097 (1995); non-ionic backbones (U.S. Pat. Nos. 5,386,023, 5,637,684, 5,602,240, 5,216,141 and 4,469,863; Kiedrowshi et al., *Angew. Chem. Intl.* Ed. English 30:423 (1991); Letsinger et al., *J. Am. Chem. Soc.* 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* 24:169–176 (1995). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, alter the hybridization properties of the nucleic acids, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

While generally described for human patients, the compositions and methods of the invention find use in detection of target sequences from a variety of sources. That is, the "target source" or source of target sample need not be limited to patients or even to humans. Indeed the method finds use in detection of target sequences from any number of sources including, plants, animals, and microorganisms such as bacteria and viruses. In a preferred embodiment the source is a mammal including humans, domestic and farm animals, and zoo, sports, or pet animals, such as dogs, cats, cattle, horses, sheep, pigs, goats, rabbits, etc. Preferably, the mammal is human. In addition, the source is a cell type, including prokaryotic or eukaryotic cells. Suitable prokaryotic cells include, but are not limited to, bacteria such as *E. coli, Bacillus* species, and the extremophile bacteria such as thermophiles, etc. Preferably, the procaryotic target cells are recombination competent. Suitable eukaryotic cells include, but are not limited to, fungi such as yeast and filamentous fungi, including species of *Aspergillus, Trichoderma,* and *Neurospora;* plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle fowl or game birds. Suitable mammalian cells include, but are not limited to, cells from horses, cattle, buffalo, deer, sheep, rabbits, rodents such as mice, rats, hamsters, gerbils, and guinea pigs, minks, goats, pigs, primates, marsupials, marine mammals including dolphins and whales, as well as cell lines, such as human cell lines of any tissue or stem cell type, and stem cells, including pluripotent and non-pluripotent, and non-human zygotes.

In addition suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

Generally, when the target nucleic acid is genomic DNA, the genomic DNA is isolated or purified from the sample. Methods for purifying genomic DNA are known in the art. For example, the sample may be treated to lyse the cells, using known lysis buffers, sonication, electroporation, etc., with purification and amplification as outlined below occurring as needed, as will be appreciated by those in the art. Once isolated, the genomic DNA is fragmented or sheared as is known. Alternatively, the genomic DNA is cleaved, for example with nucleases. In addition, genomic DNA can be prepared with commercial kits such a genomic DNA preparation kits from Qiagen or Promega, including Wizard™ Genomic DNA purification kit or ReadyAmp™ genomic DNA Purification System. Additional methods for preparing genomic DNA are outlined in U.S. Ser. No. 09/785,514, filed Feb. 16, 2001, which is expressly incorporated herein be reference.

In one embodiment the genomic DNA (gDNA) is cleaved or sheared. Preferably the gDNA is decreased in size to about 10 Kb on average. More preferably the gDNA is from 1 Kb to 50 Kb on average with from 5 Kb to 15 Kb most preferred. In a most preferred embodiment the gDNA is at least about 400 base pairs in length.

In a preferred embodiment the gDNA is substantially pure once it is immobilized on the solid support. Preferably the gDNA is purified prior to immobilization on the solid support. While it is not necessary for the gDNA to be 100% pure, in a preferred embodiment the gDNA is at least 30% pure, with at least 50% pure being more preferred and at least from 65% to 90% pure being most preferred.

In addition, the reactions using and reusing the sample material as outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, in most embodiments, double stranded target nucleic acids are denatured to render them single stranded so as to permit hybridization of the primers and other probes of the invention A preferred embodiment utilizes a thermal step, generally by raising the temperature of the reaction to about 95° C., although pH changes and other techniques may also be used.

In a preferred embodiment, the target nucleic acids or target sequences are initially immobilized on a substrate.

Attachment of the target sequences may be performed in a variety of ways, as will be appreciated by those in the art, including, but not limited to, chemical or affinity capture (for example, including the incorporation attachment moieties such as derivatized nucleotides such as AminoLink or biotinylated nucleotides that can then be used to attach the nucleic acid to a surface, as well as affinity capture by hybridization), cross-linking, and electrostatic attachment, etc. That is, an attachment moiety is attached to the target nucleic acid, i.e. genomic DNA sequences that allows for attachment to the substrate. By "attachment moiety" is meant a molecule or substance that mediates attachment of the genomic DNA to the substrate. In a preferred embodiment, affinity capture is used to attach the nucleic acids to the support. For example, nucleic acids can be derivatized, for example with one member of a binding pair, and the support derivatized with the other member, i.e. a complementary member, of a binding pair. For example, the nucleic acids may be biotinylated (for example using enzymatic incorporation of biotinylated nucleotides, or by photoactivated cross-linking of biotin). Biotinylated nucleic acids can then be captured on streptavidin-coated surfaces, as is known in the art. In a preferred embodiment the target nucleic acids are photobiotinylated with PHOTOPROBE™ Biotin Reagents (Vector Laboratories). In one embodiment the surfaces or supports are beads to which the nucleic acids are attached. In a particularly preferred embodiment the beads are magnetic beads. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Similarly, affinity capture utilizing hybridization can be used to attach nucleic acids to surface or bead. For example, a polyA tract can be attached by polymerization with terminal transferase, or via ligation of an oligoA linker, as is known in the art. This then allows for hybridization with an immobilized poly-T tract. Alternatively, chemical crosslinking may be done, for example by photoactivated crosslinking of thymidine to reactive groups, as is known in the art. In a preferred embodiment the target nucleic acids are photobiotinylated In some embodiments attachment of target nucleic acids is accomplished by hybridizing the target nucleic acids to probes that are immobilized on a solid support. That is, the immobilized probes serve to immobilize the target nucleic acids.

Attachments can be covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

A preferred embodiment utilizes covalent attachment of the target sequences to a support. As is known in the art, there are a wide variety of methods used to covalently attach nucleic acids to surfaces. A preferred embodiment utilizes the incorporation of a chemical functional group into the nucleic acid, followed by reaction with a derivatized or activated surface. Examples include, but are not limited to AminoLink.

By "substrate", "solid support", "target substrate" or "target support" or other grammatical equivalents herein is meant any material to which a target nucleic acid can be attached. The target nucleic acids can be attached either directly or indirectly as described herein. As will be appreciated by those in the art, the number of possible substrates is very large. Possible substrates include inorganic and organic substrates and are not limited to, glass and modified or functionalized glass, plastics (including acrylics, polystyrene and copolymers of styrene and other materials, polypropylene, polyethylene, polybutylene, polyurethanes, Teflon, etc.), polysaccharides, cellulose, nylon or nitrocellulose, resins, silica or silica-based materials including silicon and modified silicon, carbon, metals, inorganic glasses, plastics, and a variety of other polymers. Preferably the substrates include microfuge tubes, i.e. Eppendorf tubes. In a preferred embodiment the substrates include beads or microspheres. In one embodiment the beads or microspheres are magnetic. In one embodiment the substrates are derivatized to accommodate attachment of the target nucleic acids to the substrate.

The configuration of the target support is not crucial. What is important is that the target nucleic acids are immobilized to the target support and can be manipulated. That is, the support should be amenable to a variety of reactions as described herein. While the substrate can be flat (planar), other configurations of substrates may be used as well; for example, target nucleic acids can be attached to beads or microspheres that can be deposited in reaction tubes or vessels or wells. That is, the target substrate may be microspheres to which the target nucleic acids are attached. The microspheres can then be distributed on a surface. In some embodiments the surface contains reaction wells into which the beads are distributed, for example microtiter plates as are known in the art and as described herein. In one embodiment all of the beads to which an entire sample of target nucleic acids are attached are deposited or distributed into a single reaction well. Alternatively, a subpopulation of the beads to which a sample of target nucleic acids are attached are deposited into different wells. Generally, the subpopulation is not defined by a particular attribute, but is merely an aliquot of the complete sample of target nucleic acids immobilized to beads. In one embodiment the microspheres are magnetic particles or microspheres. These magnetic particles or beads can be immobilized with magnetic forces.

In one embodiment the target nucleic acids are immobilized into sample wells of a 96-well plate. Other formats of microtiter plates are known in the art, i.e. 384 and 1536-well plates, and find use in the invention. Alternatively, when target nucleic acids are attached to beads, the beads are distributed into sample wells of the microtiter plate. The use of microtiter plates finds particular use in the methods of the invention in that multiple target samples can be simultaneously processed. In the method of this invention, the multiple samples can be simultaneously processed sequentially. That is, as described herein, the invention provides methods of reusing target nucleic acids. When multiple samples of target nucleic acids are distributed in different sample wells of a microtiter plate, the method provides for the sequential use of a plurality of target nucleic acids simultaneously.

Once the genomic DNA is applied to or immobilized on the surface, the target sequences are contacted with probes for analyses, including detection or genotyping, of the target sequences. Accordingly, as outlined herein, the invention provides a number of different primers and probes. Probes and primers of the present invention are designed to have at least a portion be complementary to a target sequence (either the target sequence of the sample or to other probe sequences, such as portions of amplicons, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, and preferably give the required specificity.

A variety of hybridization conditions may be used in the present invention, including high, moderate and low stringency conditions; see for example Maniatis et al, Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, Part I, Chapter 2 "Overview of principles of hybridization and the strategy of nucleic acid assays," Elsevier, N.Y., 1993. Generally, stringent conditions are selected to be about 5–100° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g. 10 to 50 nucleotides) and at least about 60 C for long probes (e.g. greater than 50 nucleotides). Stringent conditions may also be achieved with the addition of helix destabilizing agents such as formainide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the first hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the primer and probe nucleic acids may vary, as will be appreciated by those in the art, with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the priming sites (including universal priming sites) of the probes are each preferably about 15–20 nucleotides in length, with 18 being especially preferred. The adapter sequences of the probes are preferably from 15–25 nucleotides in length, with 20 being especially preferred. The target specific portion of the probe is preferably from 15–50 nucleotides in length.

In some embodiments probes include priming sites for pre-amplification reactions as described below. In this embodiment, the probes include a pre-amplification priming site that is preferably positioned 5' to the universal priming site. In a preferred embodiment the pre-amplification priming site is a priming site for RNA Polymerase. Preferably the priming site is a T3 or SP6 primer. In a preferred embodiment the priming site is includes a T7 RNA primer.

Accordingly, the present invention provides first target probe sets. By "probe set" herein is meant a plurality of target probes that are used in a particular multiplexed assay. In this context, plurality means at least two, with more than 10 being preferred. More preferably the probe set includes at least 100 probes with at least 1000 probes being more preferred. In one embodiment the number of probes is at least 100 but less than 1,000,000 but is more preferably at least 200 and less than 5000. The number of probes will vary depending on the assay, sample and purpose of the test. In one embodiment the number of probes is equal to the number of genes in the genome of a particular organism to be analyzed. In some embodiments the number of probes is from one to three probes per locus or SNP to be identified. In addition, because there are generally multiple SNPs per gene, the probe sets include multiple probes per gene. That is, the probe sets include a plurality of probes for the identification or detection of a gene.

Accordingly, the invention also provides for methods of multiplexed analysis of target nucleic acids. by "multiplex" is meant the multiple analyses of a target nucleic acid. In one embodiment at least 10 analyses are performed on target nucleic acids simultaneously. In a more preferred embodiment at least 50 simultaneous analyses are performed, with at least 100 simultaneous analyses being performed. In addition, the invention provides for simultaneous analyses of at least 1000 target nucleic acids.

The target probes comprise a first target specific sequence. By "target specific" sequence is meant sequence in a probe that is substantially complementary to the target sequence. As outlined below, ligation probes each comprise a target-specific sequence. As will be appreciated by those in the art, the target-specific sequence comprises a portion that will hybridize to all or part of the target sequence and includes one or more particular single nucleotide polymorphisms (SNPs). As described above, the target specific sequence of the probe preferably are from 15–50 nucleotides in length with from 20–35 being more preferred.

In addition, the target probes comprise priming sites. By "priming sites" herein is meant a portion of the probe to which primers hybridize to form amplification templates. By amplification templates is meant a probe to which at least one amplification primer is hybridized.

Preferably the priming sites are universal priming sites. By "universal priming site" herein is meant a sequence of the probe that will bind a PCR primer for amplification. That is, all probes can contain the same universal priming site or sequence, or subsets of probes can contain the same the same universal priming site or sequence within the subset, but the priming site or sequence is distinct for different subsets. Accordingly, different subsets of probes containing the same priming sites are used for multiplexing or detecting a plurality of target sequences. That is, for example, one set of probes includes the same universal priming site, but multiple different target specific sequences. A second set of probes includes a different priming site from the first set, but the probes of the second set contain the same priming site. The probes of the second set also contain multiple different target specific sequences. As is appreciated by the skilled artisan, any number of sets can be used. In a preferred embodiment each set comprises at least 5 different target specific sequences, more preferably at least 50 different target specific sequences, with at least 100 different target specific sequences being even more preferred and up to 1,000,000 different target sequences being most preferred. That is, in some embodiments each probe set includes from 100 to 1000 different target sequences while in a most preferred embodiment each probe set includes from 100 to 10,000 different target sequences.

Each probe preferably comprises an upstream universal priming site (UUP) and a downstream universal priming site (DUP). Again, "upstream" and "downstream" are not meant to convey a particular 5'-3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In addition, the universal priming sites are preferably located at the 5' and 3' termini of the target probe (or the ligated probe), as only sequences flanked by priming sequences will be amplified. In some embodiments, for example, in the case of rolling circle embodiments, there may be a single universal priming site.

In addition, universal priming sequences are generally chosen to be as unique as possible given the particular assays and host genomes to ensure specificity of the assay. In general, universal priming sequences range in size from about 5 to about 25 basepairs, with from about 10 to about 20 being particularly preferred.

As will be appreciated by those in the art, the orientation of the two priming sites is different. That is, one PCR primer will directly hybridize to the first priming site, while the other PCR primer will hybridize to the complement of the second priming site. Stated differently, the first priming site is in sense orientation, and the second priming site is in antisense orientation.

In a preferred embodiment the invention is directed to methods of detecting target sequences that comprise one or more positions for which sequence information is desired, generally referred to herein as the "detection position" or "detection locus". In a preferred embodiment, the detection position is a single nucleotide (sometimes referred to as a single nucleotide polymorphism (SNP)), although in some embodiments, it may comprise a plurality of nucleotides, either contiguous with each other or separated by one or more nucleotides. By "plurality" as used herein is meant at least two. As used herein, the base of a probe (e.g. the target probe) which basepairs with a detection position base in a hybrid is termed a "readout position" or an "interrogation position". Thus, the target sequence comprises a detection position and the target probe comprises a readout position. In general, this embodiment utilizes the OLA or RCA assay, as described below.

Thus, in a preferred embodiment, genotyping reactions are performed on the immobilized DNA. These genotyping techniques fall into four general categories: (1) techniques that rely on traditional hybridization methods that utilize the variation of stringency conditions (temperature, buffer conditions, etc.) to distinguish nucleotides at the detection position; (2) extension techniques that add a base ("the readout base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques that also rely on enzymatic or chemical specificity such that cleavage occurs preferentially if perfect complementarity exists and (5) techniques that combine these methods.

As will be appreciated by those in the art, the reactions described below can take on a wide variety of formats. In one embodiment, genomic DNA is attached to a solid support, and probes comprising priming sites are added to form hybridization complexes, in a variety of formats as outlined herein. The non-hybridized probes are then removed, and the hybridization complexes are denatured. This releases the probes (which frequently have been altered in some way). The probes are then amplified and detected, for example upon addition to an array of capture probes. Several embodiments of this have been described above. Alternatively, genomic DNA is attached to a solid support, and genotyping reactions are done in formats that can allow amplification as well, either during the genotyping reaction (e.g. through the use of heat cycling) or after, without the use of universal primers. Thus, for example, when labeled probes are used, they can be hybridized to the immobilized genomic DNA, unbound materials removed, and then eluted and collected to be added to arrays. This may be repeated for amplification purposes, with the elution fractions pooled and added to the array. In addition, alternative amplification schemes such as extending a product of the invasive cleavage reaction (described below) to include universal primers or universal primers and adapters can be performed. In one embodiment this allows the reuse of immobilized target sequences with a different set or sets of target probes.

Simple Hybridization Detection or Genotyping

In a preferred embodiment, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

Competitive Hybridization

In a preferred embodiment, the use of competitive hybridization probes (generally referred to herein as "readout probes") is performed to elucidate either the identity of the nucleotide(s) at the detection position or the presence of a mismatch. Readout probes also are known as target probes or target readout probes as described herein. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "match" and "mismatch". Thus, the present invention may be used to detect substitutions, insertions or deletions as compared to a wild-type sequence. In general, probes of the present invention are designed to be complementary to a target sequence, such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

In a preferred embodiment, a plurality of probes (sometimes referred to herein as "readout probes", "detection probes", "target probes" or "target readout probes") are used to identify the base at the detection position. In this embodiment, each different readout probe comprises a different detection label (which, as outlined below, can be either a primary label or a secondary label) and a different base at the position that will hybridize to the detection position of the target sequence (herein referred to as the readout position) such that differential hybridization will occur (see FIG. 1) That is, all other parameters being equal, a perfectly complementary readout probe (a "match probe") will in general be more stable and have a slower off rate than a probe comprising a mismatch (a "mismatch probe") at any particular temperature. Accordingly, by using different readout probes, each with a different base at the readout position and each with a different label, the identification of the base at the detection position is elucidated.

In one embodiment the readout probes are the same length. Preferably the probes have a similar melting temperature (Tm), although this is not required. In an alternative embodiment, readout probes as described herein need not be of the same length. That is, readout probes can be of different lengths. Using readout probes of different lengths provides the advantage that in varying the length of the probes, the Tm of the probes can be adjusted. This is beneficial in allowing uniform assay conditions can be used.

In one embodiment the readout probes comprise a detection label. By "detection label" or "detectable label" herein is meant a moiety that allows detection. This may be a primary label (which can be directly detected) or a secondary label (which is indirectly detected).

A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methylcoumarins, quantum dots (also referred to as "nanocrystals"), pyrene, Malacite green, stilbene, Lucifer Yellow, Cascade Blue™, Cy dyes (Cy3, Cy5, etc.), Texas Red, phycoerythrin, Bodipy, Alexa dyes and others described in the 6th Edition of the Molecular Probes Handbook by Richard P. Haugland, hereby expressly incorporated by reference. In a preferred embodiment, the detection label used for competitive hybridization is a primary label.

In a preferred embodiment, the detectable label is a secondary label. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage, etc. reactions; in addition, these techniques may be used with many of the other techniques described herein. Secondary labels include, but are not limited to, one of a binding partner pair; chemically modifiable moieties; nuclease inhibitors, enzymes such horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin and digoxygenin and antibodies; enzymes and substrates or inhibitors; other protein-protein interacting pairs; receptor-ligands; and carbohydrates and their binding partners, are also suitable binding pairs. Nucleic acid- nucleic acid binding proteins pairs are also useful. In general, the smaller of the pair is attached to the NTP (or the probe) for incorporation into the extension primer. Preferred binding partner pairs include, but are not limited to, biotin (or imino-biotin) and streptavidin, digeoxinin and Abs, and Prolinx™ reagents (see www.prolinxinc com/ie4/home.hmtl).

In a preferred embodiment, the binding partner pair comprises a primary detection label (attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$–$10^{-6}$ M–$^1$, with less than about $10^{-5}$ to $10^{-9}$ M$^{-1}$ being preferred and less than about $10^{-7}$–$10^{-9}$ M–$^1$ being particularly preferred.

In addition, the secondary label can be a chemically modifiable moiety. In this embodiment, labels comprising reactive functional groups are incorporated into the nucleic acid. Subsequently, primary labels, also comprising functional groups, may be added to these reactive groups. As is known in the art, this may be accomplished in a variety of ways. Preferred functional groups for attachment are amino groups, carboxy groups, oxo groups and thiol groups, with amino groups being particularly preferred. Using these functional groups, the primary labels can be attached using functional groups on the enzymes. For example, primary labels containing amino groups can be attached to secondary labels comprising amino groups, for example using linkers as are known in the art; for example, homo-or heterobifunctional linkers as are well known (see 1994 Pierce Chemical Company catalog, technical section on crosslinkers, pages 155–200, incorporated herein by reference).

Accordingly, in some embodiments a detectable label is incorporated into the readout probe. In a preferred embodiment, a set of readout probes are used, each comprising a different base at the readout position. In some embodiments, each readout probe comprises a different label, that is distinguishable from the others. For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

The number of readout probes used will vary depending on the end use of the assay. For example, many SNPs are biallelic, and thus two readout probes, each comprising an interrogation base that will basepair with one of the detection position bases. For sequencing, for example, for the discovery of SNPs, a set of four readout probes are used.

In one embodiment labels are not incorporated into the readout probes. Rather, the readout probes are used as a template for subsequent amplification reactions described in more detail below. Generally, in this embodiment the readout probe includes priming sequences as described herein and a label is incorporated into the amplification product, i.e. the amplicon. As described above, the label may be either direct or indirect.

Accordingly, the method includes adding target readout probes to target nucleic acids that are immobilized on a surface. Unbound probes are washed away or removed from the complex. The bound probes are then removed, i.e. denatured, from the complex and collected. In a preferred embodiment, a second set of readout probes is then added to the immobilized target nucleic acids. The immobilized target nucleic acids can be reused indefinitely as described below. In one embodiment the readout probes contain a label. In an alternative embodiment the readout probes contain priming sequences and are amplified. Labels are incorporated into the amplification products (amplicons). Finally, the identity of the isolated probes or amplicons is determined by contacting the probes with an array as described below.

Stringency Variation

In a preferred embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occuring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art; see for example Maniatis et al., Molecular Cloning:

A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

As will be appreciated by those in the art, mismatch detection using temperature may proceed in a variety of ways, and is similar to the use of readout probes as outlined above. Again, as outlined above, a plurality of readout probes may be used in a sandwich format; in this embodiment, all the probes may bind at permissive, low temperatures (temperatures below the Tm of the mismatch); however, repeating the assay at a higher temperature (above the Tm of the mismatch) only the perfectly matched probe may bind. Thus, this system may be run with readout probes with different detectable labels, as outlined above. Alternatively, a single probe may be used to query whether a particular base is present.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of $\leq 40\%$. Low stringency conditions include NaCl concentrations of $\geq 1$ M, and high stringency conditions include concentrations of $\leq 0.3$ M. Furthermore, low stringency conditions include $MgCl_2$ concentrations of $\geq 10$ mM, moderate stringency as 1–10 mM, and high stringency conditions include concentrations of $\leq 1$ mM.

In this embodiment, as for temperature, a plurality of readout probes may be used, with different bases in the readout position (and optionally different labels). Running the assays under the permissive conditions and repeating under stringent conditions will allow the elucidation of the base at the detection position.

Accordingly, the method includes adding target readout probes to target nucleic acids that are immobilized on a surface. Complexes are formed under permissive conditions, followed by increasing the stringency which results in release of the mismatched probe. Unbound probes are washed away or removed from the complex. The bound probes are then removed, i.e. denatured, from the complex and collected. In a preferred embodiment, a second set of readout probes are then added to the immobilized target nucleic acids. The target nucleic acids can be reused indefinitely as described below. In one embodiment the readout probes contain a label. In an alternative embodiment the readout probes contain priming sequences and are amplified. Labels are incorporated into the amplification products (amplicons). Finally, the identity of the isolated probes or amplicons is determined by contacting the probes with an array as described below.

Extension Genotyping

In this embodiment, any number of techniques are used to add a nucleotide to the readout position of an extension probe. By "extension probe" is meant a probe hybridized to the target sequence adjacent to the detection position. Extension probes also are included in the definition of readout probes or target probes. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

Single Base Extension

In one embodiment, single base extension (SBE; sometimes referred to as "minisequencing") is used to determine the identity of the base at the detection position. Briefly, SBE is a technique that utilizes an extension primer (also included withing the definition of readout probe) that hybridizes to the target nucleic acid immediately adjacent to the detection position. A polymerase (generally a DNA polymerase) is used to extend the 3' end of the primer with a nucleotide analog labeled a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein. See generally Sylvanen et al., Genomics 8:684–692 (1990); U.S. Pat. Nos. 5,846,710 and 5,888,819; Pastinen et al., Genomics Res. 7(6):606–614 (1997); all of which are expressly incorporated herein by reference.

The reaction is initiated by contacting the assay complex comprising the immobilized target sequence (i.e. the array) to a solution comprising a first nucleotide. By "nucleotide" in this context herein is meant a deoxynucleoside-triphosphate (also called deoxynucleotides or dNTPs, e.g. dATP, dTTP, dCTP and dGTP). In general, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required.

In a preferred embodiment, the nucleotide analogs comprise a detectable label, which can be either a primary or secondary detectable label. Preferred primary labels are those outlined above for interrogation labels. However, the enzymatic incorporation of nucleotides comprising fluorophores is may be poor under many conditions; accordingly, a preferred embodiment utilizes secondary detectable labels. In addition, as outlined below, the use of secondary labels may also facilitate the removal of unextended probes.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

In addition to a first nucleotide, the solution also comprises an extension enzyme, generally a DNA polymerase. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. If the NTP is complementary to the base of the detection position of the target sequence, which is adjacent to the extension primer, the extension enzyme will add it to the extension primer at the readout position. Thus, the extension primer is modified, i.e. extended, to form a modified primer, sometimes referred to herein as a "newly synthesized strand". If desired, the temperature of the reaction can be adjusted (or cycled) such that amplification occurs, generating a plurality of modified primers.

In addition, since unextended primers do not comprise labels, the unextended primers need not be removed. However, they may be, if desired, as outlined below; for example, if a large excess of primers are used, there may not be sufficient signal from the extended primers competing for binding to the surface. In addition, removal of unextended primers is desirable when extended primers are to be amplified. That is, when amplification follows an extension reaction, it is desirable to remove the unextended primers so that they are also not amplified.

As will be appreciated by those in the art, the determination of the base at the detection position can proceed in several ways. In a preferred embodiment, the reaction is run with all four nucleotides (assuming all four nucleotides are required), each with a different label, as is generally outlined herein. Alternatively, a single label is used, by using four reactions: this may be done either by using a single substrate and sequential reactions, or by using a sample divided into four reaction wells. For example, dATP can be added to the assay complex, and the generation of a signal evaluated; the dATP can be removed and dTTP added, etc. Alternatively, four reaction wells can be used; the first well includes dATP, the second includes dTTP, etc., and the presence or absence of a signal evaluated.

Alternatively, ratiometric analysis can be done; for example, two labels, "A" and "B", on two substrates (e.g. two reaction wells) can be done. In this embodiment, two sets of primer extension reactions are performed, each in two wells, with each reaction containing a complete set of four chain terminating NTPs. The first reaction contains two "A" labeled nucleotides and two "B" labeled nucleotides (for example, A and C may be "A" labeled, and G and T may be "B" labeled). The second reaction also contains the two labels, but switched; for example, A and G are "A" labeled and T and C are "B" labeled. Following the reaction, the modified primers are removed from the immobilized target nucleic acid and analyzed on a bead array as described below. In a preferred embodiment the modified probes from each reaction are contacted or immobilized on separate beads as described below and detected on a bead array. This reaction allows a biallelic marker to be ratiometrically scored; that is, the intensity of the two labels in two different "color" channels on a single bead is compared, using data from a set of two hybridized arrays. For instance, if the marker is A/G, then the first reaction on the first bead is used to calculate a ratiometric genotyping score; if the marker is A/C, then the second reaction on the second bead is used for the calculation; if the marker is G/T, then the second bead is used, etc. This concept can be applied to all possible biallelic marker combinations "Scoring" a genotype using a single bead ratiometric score allows a much more robust genotyping than scoring a genotype using a comparison of absolute or normalized intensities between two different arrays.

As will be appreciated by the skilled artisan, while SBE is a powerful technique for determining the nucleotide at the detection position of a target nucleic acid, the labeled target probe can not amplified with universal primers in this configuration. That is, while specific primers can be used to amplify the modified target probe, universal primers are not as there are not primers that are upstream and downstream of the detection position. When specific primers are used, a label can be incorporated into the amplicon as described herein. In addition, the product of the reaction can be "pre-amplified" as described herein. Thus, by reusing the original sample DNA, sample preparation for this and other assays is greatly simplified.

Although straight SBE is not amenable to amplification with universal primers, a configuration that does allow for amplification with universal primers is SBE followed by oligonucleotide ligation assay (OLA), i.e. the Genetic Bit Assay. OLA is described in more detail below. In this embodiment, an extension probe is hybridized to the target nucleic acids and the SBE reaction is performed as described above. Extension probe also is included in the definition of target probe as defined herein. In addition, an upstream ligation probe is hybridized to the target nucleic acid. The upstream ligation probe hybridizes to the target nucleic acid immediately adjacent to the detection position. Following incorporation of the appropriate nucleotide into the extension probe as a result of the SBE reaction, the complex is contacted with a ligase that only ligates the modified extension probe and upstream ligation probe when the correct nucleotide has been incorporated into the extension probe. Following ligation, the ligated probe is removed from the target nucleic acid and either directly detected on an array as described below, or amplified. When the ligated probe is to be amplified, preferably the target probes, i.e. either the upstream ligation primer or extension primer contain priming sites for amplification primers. In a preferred embodiment the priming sites are universal priming sties as described herein.

Once the assay is complete and the extended probe (when SBE is used) or the ligated probe (when Genetic bit is used)

are removed from the target nucleic acid, the target nucleic acid can be reused as described herein. That is, the immobilized target nucleic acid can be contacted with a subsequent set of probes for additional analyses.

Allelic PCR

In a preferred embodiment, the method used to detect the base at the detection position is allelic PCR, referred to herein as "aPCR". As described in Newton et al., Nucl. Acid Res. 17:2503 (1989), hereby expressly incorporated by reference, allelic PCR allows single base discrimination based on the fact that the PCR reaction does not proceed well if the terminal 3'-nucleotide is mismatched, assuming the DNA polymerase being used lacks a 3'-exonuclease proofreading activity. Accordingly, the identification of the base proceeds by using allelic PCR primers (sometimes referred to herein as aPCR primers) that have readout positions at their 3' ends. aPCR primers also are included within the definition of readout probes or target probes. Thus the target sequence comprises a first domain comprising at its 5' end a detection position.

In general, aPCR may be briefly described as follows. A target nucleic acid is immobilized on a substrate as described herein. The target nucleic acid is then denatured, generally by raising the temperature, and then cooled in the presence of an excess of a aPCR primer, which then hybridizes to the first target strand. If the readout position of the aPCR primer basepairs correctly with the detection position of the target sequence, a DNA polymerase (again, that lacks 3'-exonuclease activity) then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. In one embodiment the dissociated extended primer is removed from the immobilized target nucleic acid prior to subsequent amplification cycles, although this is not required. When the extended primer is removed from the immobilized target the target can be reused with a different set of primers. Alternatively, a different assay can be performed on the same target nucleic acid. Thus aPCR steps are denaturation, annealing and extension. The particulars of aPCR are well known, and include the use of a thermostable polymerase such as Taq I polymerase and thermal cycling.

Accordingly, the aPCR reaction requires at least one aPCR primer, a polymerase, and a set of dNTPs. As outlined herein, the primers may comprise the label, or one or more of the dNTPs may comprise a label. As described above for SBE, when only one aPCR primer is used, amplification with universal primers will not occur. However, when two a PCR primers are used, each of the primers contains a priming site upstream of the target sequence. During each cycle of aPCR, the resulting extended product contains not only the amplified target sequence, but also the sequence of each of the primers flanking the target specific sequences. As such, universal primers can be used to amplify the product.

It should be noted in this embodiment, at least one cycle of amplification with two aPCR primers is required in order to generate a product that contains two priming sites. Again, preferably the priming sites are universal priming sites.

Furthermore, the aPCR reaction may be run as a competition assay of sorts. For example, for biallelic SNPs, a first aPCR primer comprising a first base at the readout position and a first label, and a second aPCR primer comprising a different base at the readout position and a second label, may be used. The PCR primer for the other strand is the same. The examination of the ratio of the two colors can serve to identify the base at the detection position.

The amplicons produced by the aPCR reaction and subsequent universal amplification steps can be analyzed on an array as described below. In addition, the immobilized target nucleic acid can be reused in a subsequent aPCR reaction or different detection or genotyping reaction as described herein.

Ligation Techniques for Genotyping

In this embodiment, the readout of the base at the detection position proceeds using a ligase. In this embodiment, it is the specificity of the ligase which is the basis of the genotyping; that is, ligases generally require that the 5' and 3' ends of the ligation probes have perfect complementarity to the target for ligation to occur. Ligation probes also are included within the definition of readout probes or target probes.

In a preferred embodiment, the identity of the base at the detection position proceeds utilizing the OLA. The method can be run at least two different ways; in a first embodiment, only one strand of a target sequence is used as a template for ligation; alternatively, both strands may be used; the latter is generally referred to as Ligation Chain Reaction or LCR. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, and U.S. Ser. Nos. 60/078,102 and 60/073,011, all of which are incorporated by reference.

This method is based on the fact that two probes can be preferentially ligated together, if they are hybridized to a target strand and if perfect complementarity exists at the two bases being ligated together. Thus, in this embodiment, the immobilized target sequence comprises a contiguous first target domain comprising the detection position and a second target domain adjacent to the detection position. That is, the detection position is "between" the rest of the first target domain and the second target domain. A first ligation probe is hybridized to the first target domain and a second ligation probe is hybridized to the second target domain. If the first ligation probe has a base perfectly complementary to the detection position base, and the adjacent base on the second probe has perfect complementarity to its position, a ligation structure is formed such that the two probes can be ligated together to form a ligated probe. If this complementarity does not exist, no ligation structure is formed and the probes are not ligated together to an appreciable degree. In addition, as is more fully outlined herein, this method may also be done using ligation probes that are separated by one or more nucleotides, if dNTPs and a polymerase are added (this is sometimes referred to as "Genetic Bit" analysis).

In a preferred embodiment, LCR is done for two strands of a double-stranded target sequence. The immobilized target sequence is denatured, and two sets of probes are added: one set as outlined above for one strand of the target, and a separate set (i.e. third and fourth primer probe nucleic acids) for the other strand of the target, both of which are part of a particular target set.

As will be appreciated by those in the art, the ligation product can be detected in a variety of ways. Preferably, detection is accomplished by removing the unligated labeled probe from the reaction.

Preferably, after the OLA assay is performed, the unligated oligonucleotides are removed by washing under appropriate stringency to remove unligated oligonucleotides. In one embodiment, one of the probes comprises a label, which is detected on an array as described herein. In a preferred embodiment the ligation product is amplified to produce an amplicon; preferably a label is incorporated into the amplicon as described herein. In a preferred embodiment the ligation probes comprise priming sites for amplification as described herein. That is, flaking the target specific sequence of both of the ligation probes the probes include priming sequences. The priming sequences allow for amplification of the ligated probe. In a preferred embodiment the priming sequences are universal priming sequences as described herein.

In one embodiment, once the ligated probe is removed from the immobilized target nucleic acid, the target nucleic acid is reused in a subsequent analysis, i.e. detection or genotyping assay, as described herein. The ligated probe, or amplicon resulting from the amplification reaction, is detected on an array as described below.

Padlock Probe Ligation

In a preferred embodiment, the ligation probes are specialized probes called "padlock probes" (which also are within the definition of readout probes) Nilsson et al, 1994, Science 265:2085. These probes have a first ligation domain that is identical to a first ligation probe, in that it hybridizes to a first target sequence domain, and a second ligation domain, identical to the second ligation probe, that hybridizes to an adjacent target sequence domain. Again, as for OLA, the detection position can be either at the 3' end of the first ligation domain or at the 5' end of the second ligation domain. However, the two ligation domains are connected by a linker, frequently nucleic acid. The configuration of the system is such that upon ligation of the first and second ligation domains of the padlock probe, the probe forms a circular probe, and forms a complex with the target sequence wherein the target sequence is "inserted" into the loop of the circle.

In this embodiment, the unligated probes may be removed through degradation (for example, through a nuclease), as there are no "free ends" in the ligated probe.

In a preferred embodiment the "padlock probe" contains a priming site for amplification. Preferably the priming site is located in the "linker" region of the padlock probe. Only one priming site is required as amplification proceeds around the closed circle resulting in a single amplicon containing multiple copies of the probe sequence. In a preferred embodiment the padlock probe contains with its sequence a restriction site. As such, following amplification of the probe sequence, the amplicon can be cleaved resulting in multiple segments of amplicon DNA containing the sequence of the padlock probe. Following cleavage, the cleaved amplicon products can be detected on an array as described herein.

Following removal of the padlock probe from the immobilized target nucleic acid, the immobilized target nucleic acid can be used for subsequent analyses including detection and genotyping analysis.

Cleavage Techniques for Genotyping

In a preferred embodiment, the specificity for genotyping is provided by a cleavage enzyme There are a variety of enzymes known to cleave at specific sites, either based on sequence specificity, such as restriction endonucleases, or using structural specificity, such as is done through the use of invasive cleavage technology.

Endonuclease Techniques

In a preferred embodiment, enzymes that rely on sequence specificity are used. In general, these systems rely on the cleavage of double stranded sequence containing a specific sequence recognized by a nuclease, preferably an endonuclease including resolvases.

These systems may work in a variety of ways, as outlined in U.S. Ser. No. 09/556,463, filed Apr. 21, 2000, which is expressly incorporated herein by reference. In one embodiment, a labeled readout probe is used; the binding of the target sequence forms a double stranded sequence that a restriction endonuclease can then recognize and cleave, if the correct sequence is present. The cleavage results in the loss of the label, and thus a loss of signal.

Alternatively, as will be appreciated by those in the art, a labelled target sequence may be used as well; for example, a labelled primer may be used in the PCR amplification of the target, such that the label is incorporated in such a manner as to be cleaved off by the enzyme.

Alternatively, the readout probe (or, again, the target sequence) may comprise both a fluorescent label and a quencher, as is known in the art. In this embodiment, the label and the quencher are attached to different nucleosides, yet are close enough that the quencher molecule results in little or no signal being present. Upon the introduction of the enzyme, the quencher is cleaved off, leaving the label, and allowing signalling by the label.

In addition, as will be appreciated by those in the art, these systems can be both solution-based assays or solid-phase assays, as outlined herein.

Furthermore, there are some systems that do not require cleavage for detection; for example, some nucleic acid binding proteins will bind to specific sequences and can thus serve as a secondary label. For example, some transcription factors will bind in a highly sequence dependent manner, and can distinguish between two SNPs. Having bound to the hybridization complex, a detectable binding partner can be added for detection. In addition, mismatch binding proteins based on mutated transcription factors can be used.

In addition, as will be appreciated by those in the art, this type of approach works with other cleavage methods as well, for example the use of invasive cleavage methods, as outlined below.

Invasive Cleavage

In a preferred embodiment, the determination of the identity of the base at the detection position of the target sequence proceeds using invasive cleavage technology. As outlined above for amplification, invasive cleavage techniques rely on the use of structure-specific nucleases, where the structure can be formed as a result of the presence or absence of a mismatch Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". The non-complementary end of the second probe preferably comprises a "generic" or "unique" sequence, frequently referred to herein as a "detection sequence", that is used to indicate the presence or absence of the target nucleic acid, as described below. The detection sequence of the second probe preferably comprises at least one detectable label. Alternative methods have the detection sequence functioning as a target sequence for a capture probe, and thus rely on sandwich configurations using label probes.

Hybridization of the first and second oligonucleotides near or adjacent to one another on the target nucleic acid forms a number of structures. In a preferred embodiment, a forked cleavage structure forms and is a substrate of a nuclease which cleaves the detection sequence from the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

As above, the invasive cleavage assay is preferably performed on an array format. In a preferred embodiment, the signal probe has a detectable label, attached 5' from the site of nuclease cleavage (e.g. within the detection sequence) and a capture tag, as described herein for removal of the unreacted products (e.g. biotin or other hapten) 3' from the site of nuclease cleavage. After the assay is carried out, the uncleaved probe and the 3' portion of the cleaved signal probe (e.g. the the detection sequence) may be extracted, for example, by binding to streptavidin beads or by crosslinking through the capture tag to produce aggregates or by antibody to an attached hapten. By "capture tag" herein is a meant one of a pair of binding partners as described above, such as antigen/antibody pairs, digoxygenenin, dinitrophenol, etc.

The cleaved 5' region, e.g. the detection sequence, of the signal probe, comprises a label and is detected and optionally quantitated. In one embodiment, the cleaved 5' region is hybridized to a probe on an array (capture probe) and optically detected. As described below, many different signal probes can be analyzed in parallel by hybridization to their complementary probes in an array. In a preferred embodiment, combination techniques are used to obtain higher specificity and reduce the detection of contaminating uncleaved signal probe or incorrectly cleaved product, an enzymatic recognition step is introduced in the array capture procedure. For example, as more fully outlined below, the cleaved signal probe binds to a capture probe to produce a double-stranded nucleic acid in the array. In this embodiment, the 3' end of the cleaved signal probe is adjacent to the 5' end of one strand of the capture probe, thereby, forming a substrate for DNA ligase (Broude et al. 1991. PNAS 91: 3072–3076). Only correctly cleaved product is ligated to the capture probe. Other incorrectly hybridized and non-cleaved signal probes are removed, for example, by heat denaturation, high stringency washes, and other methods that disrupt base pairing.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe (the "invader probe") is hybridized to the first target domain of the target sequence. A second probe (the "signal probe"), comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signalling probe. This then can be used as a target sequence in an assay complex.

In addition, as for a variety of the techniques outlined herein, unreacted probes (i.e. signaling probes, in the case of invasive cleavage), may be removed using any number of techniques. For example, the use of a binding partner coupled to a solid support comprising the other member of the binding pair can be done. Similarly, after cleavage of the primary signal probe, the newly created cleavage products can be selectively labeled at the 3' or 5' ends using enzymatic or chemical methods.

Again, as outlined above, the detection of the invasive cleavage reaction can occur directly, in the case where the detection sequence comprises at least one label, or indirectly, using sandwich assays, through the use of additional probes; that is, the detection sequences can serve as target sequences, and detection may utilize amplification probes, capture probes, capture extender probes, label probes, and label extender probes, etc.

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signalling probe, and a cleavage enzyme.

As for other methods outlined herein, the invasive cleavage reaction may be done as a solution based assay or a solid phase assay.

Solution-based Invasive Cleavage

The invasive cleavage reaction may be done in solution, followed by addition of one of the components to an array, with optional (but preferable) removal of unreacted probes. For example, the reaction is carried out in solution, using a capture tag (i.e. a member of a binding partner pair) that is separated from the label on the detection sequence with the cleavage site. After cleavage (dependent on the base at the detection position), the signaling probe is cleaved. The capture tag is used to remove the uncleaved probes (for example, using magnetic particles comprising the other member of the binding pair), and the remaining solution is added to the array. In this embodiment, the detection sequence can effectively act as an adapter sequence. In alternate embodiments, the detection sequence is unlabelled and an additional label probe is used; as outlined below, this can be ligated to the hybridization complex.

Solid-phase Based Assays

The invasive cleavage reaction can also be done as a solid-phase assay. The target sequence can be attached to the array using a capture probe (in addition, although not shown, the target sequence may be directly attached to the array). In a preferred embodiment, the signalling probe comprises both a fluorophore label (attached to the portion of the signalling probe that hybridizes to the target) and a quencher (generally on the detection sequence), with a cleavage site in between. Thus, in the absence of cleavage, very little signal is seen due to the quenching reaction. After cleavage, however, the detection sequence is removed, along with the quencher, leaving the unquenched fluorophore. Similarly, the invasive probe may be attached to the array.

In a preferred embodiment, the invasive cleavage reaction is configured to utilize a fluorophorequencher reaction. A signaling probe comprising both a fluorophore and a quencher is attached to the bead. The fluorophore is contained on the portion of the signaling probe that hybridizes to the target sequence, and the quencher is contained on a portion of the signaling probe that is on the other side of the cleavage site (termed the "detection sequence" herein). In a preferred embodiment, it is the 3' end of the signaling probe that is attached to the bead (although as will be appreciated by those in the art, the system can be configured in a variety of different ways, including methods that would result in a loss of signal upon cleavage). Thus, the quencher molecule is located 5' to the cleavage site. Upon assembly of an assay complex, comprising the target sequence, an invader probe, and a signalling probe, and the introduction of the cleavage enzyme, the cleavage of the complex results in the disassociation of the quencher from the complex, resulting in an increase in fluorescence.

In this embodiment, suitable fluorophore-quencher pairs are as known in the art. For example, suitable quencher molecules comprise Dabcyl.

Pre-Amplification of Detection or Genotyping Products

In one embodiment, the probes include a pre-amplification priming site. The pre-amplification priming sites contain sites to which primers for DNA or RNA polymerases will hybridize. As described above, DNA polymerases or RNA polymerases can be used, although RNA polymerases are preferred.

When RNA polymerases are used, the pre-amplification priming sites include a priming site for the RNA polymerase. Preferred primer sequences include but are not limited to SP6, T3 or T7 primers. T7 is the preferred primer.

In one embodiment, the pre-amplification priming site is positioned upstream of the upstream priming site or UUP when universal priming sites are used for amplification. In addition, only one pre-amplification priming site is necessary. That is, for example, when SBE is used, only one pre-amplification priming site need be included in the target probe. When OLA is used, which requires two ligation probes, only one of the ligation probes need contain a pre-amplification priming site, although both ligation probes can contain one. When both ligation probes contain one, the pre-amplification priming site in the downstream priming site should be positioned downstream of the downstream priming site. That is, when two pre-amplification priming sites are used, they should be positioned such that they flank both the target specific sequence and the upstream and downstream priming sites. As such, upon complection of a pre-amplification reaction, all of the intervening sequences, including the priming sites are amplified.

Amplification

Following either the initial detection or genotyping reaction or the pre-amplification reaction, the products of the respective reaction are amplified. Preferred methods of amplification include the polymerase chain reaction (PCR) or rolling circle amplification (RCA) as is known in the art. Methods include contacting the reaction products with primers that hybridize to the priming sites that are included in the initial target probe. That is, the initial target probe contains priming sites, preferably universal priming sites for the amplification of the products. Accordingly, the amplification primers are universal primers; that is the primers to amplify the different detection or genotyping products contain the same sequence.

In a preferred embodiment, the amplification technique is PCR. The polymerase chain reaction (PCR) is widely used and described, and involves the use of primer extension combined with thermal cycling to amplify a the product of a genotyping or detection assay, or the product of a pre-amplification reaction; see U.S. Pat. Nos. 4,683,195 and 4,683,202, and PCR Essential Data, J. W. Wiley & sons, Ed. C. R. Newton, 1995, all of which are incorporated by reference. For clarity, these reaction products are referred to herein as amplification templates.

In general, PCR may be briefly described as follows. The double stranded amplification template is denatured, generally by raising the temperature, and then cooled in the presence of an excess of a PCR primer, which then hybridizes to the first priming site, i.e. universal priming site when universal priming sites are included in the initial target probe(s). A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second universal priming site, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase.

The reaction is initiated by contacting the amplification templates with a solution comprising the primers (universal primers when applicable), a polymerase and a set of nucleotides. By "nucleotide" in this context herein is meant a deoxynucleoside-triphosphate (also called deoxynucleotides or dNTPs, e.g. dATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction requires at least one PCR primer, a polymerase, and a set of dNTPs. As outlined herein, the primers may comprise the label, or one or more of the dNTPs may comprise a label.

In a preferred embodiment, the methods of the invention include a rolling circle amplification (RCA) step. This may be done in several ways. In one embodiment, either single target probes or ligated probes can be used in the detection or genotyping part of the assay as described above, followed by RCA instead of PCR. That is, RCA is used to amplify the product of the detection or genotyping reaction or pre-amplification reaction. Alternatively, and more preferably, the RCA reaction forms part of the genotyping reaction as described above and can be used for both detection or genotyping and amplification in the methods of the reaction.

In a preferred embodiment, the methods rely on rolling circle amplification. "Rolling circle amplification" is based on extension of a circular probe that has hybridized to a target sequence when used in the detection or genotyping reaction, or amplification templates when amplifying the products of the reaction. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) *Nuc. Acids Res.* 26:5073–5078; Barany, F. (1991) *Proc. Natl. Acad. Sci. USA* 88:189–193; and Lizardi et al. (1998) *Nat. Genet.* 19:225–232, all of which are incorporated by reference in their entirety.

Labeling of the amplicon can be accomplished in a variety of ways; for example, the polymerase may incorporate labeled nucleotides, or alternatively, a label probe is used that is substantially complementary to a portion of the RCA probe and comprises at least one label is used, as is generally outlined herein.

The polymerase can be any polymerase, but is preferably one lacking 3' exonuclease activity (3' exo). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labelled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, e.g. is a universal priming site, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

In a preferred embodiment the RCA is performed in solution followed by restriction endonuclease cleavage of the RCA product. The cleaved product is then applied to an array comprising beads, each bead comprising a probe complementary to the adapter sequence located in the padlock probe or complementary to the target specific sequence. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

Thus, the present invention provides for the generation of amplicons.

In a preferred embodiment, the amplicons are labeled with a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair such as biotin/streptavidin; chemically modifiable moieties; nuclease inhibitors, enzymes such as horseradish peroxidase, alkaline phosphatases, lucifierases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the amplicon) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference).

As outlined herein, labeling can occur in a variety of ways, as will be appreciated by those in the art. In general, labeling can occur in one of three ways: labels are incorporated into primers such that the amplification reaction results in amplicons that comprise the labels; labels are attached to dNTPs and incorporated by the polymerase into the amplicons; or the amplicons comprise a label sequence that is used to hybridize a label probe, and the label probe comprises the labels. It should be noted that in the latter case, the label probe can be added either before the amplicons are contacted with an array or afterwards.

A preferred embodiment utilizes one primer comprising a biotin, that is used to bind a fluorescently labeled streptavidin.

Re-use of Target Nucleic Acids

Upon completion of a first round of analyses, i.e. detection or genotyping, the modified probes are removed from the target nucleic acids as described above. Once removed, the immobilized target nucleic acids are contacted with a second set of target probes for subsequent analyses. That is, the invention provides methods of reusing immobilized target nucleic acids.

Re-using immobilized target nucleic acids has a number of advantages. First, the method maximizes the information obtained from a single sample or starting material. Accordingly, the invention provides a method of increasing the information obtained from an immobilized target nucleic acid. As described above, the method includes performing a first analysis with a first probe or probe set, removing the modified probe(s) and performing a second analysis with a second probe or probe set. While there is no theoretical limit to the number of reactions or reiterative uses performed on an immobilized target, in one embodiment the target nucleic acid is re-used at least twice, more preferably at least 10 times, and most preferably at least 20 times.

In a preferred embodiment, the signal obtained from subsequent analyses is not diminished when compared to the first reaction, although in some instances the signal is reduced. Preferably the signal is not reduced more than 40%, with not more than 20% more preferred and not more than 10% most preferred. That is, when comparing a signal from a second analysis with the signal from the first analysis, the signal from the second preferably is not less than 60% of that obtained from the first, more preferably not less than 80% less than the signal from the first and most preferably not less than 90% of that obtained from the first signal. In a preferred embodiment, the signal from each successive analysis is not diminished relative to the signal obtained from the previous assay.

Detection of Amplicons

Once removed from the target sequence and after the optional amplification and/or pre-amplification procedure described above, the probe or probes from either the first or any of the subsequent assays as described above or the amplicons are analyzed to detect the product and/or identify the nucleotide at the detection position of the target sequence. That is, the above described genotyping assays or amplification assays results in the production of modified target probes as an indication of the nucleotide at the detection position of target sequence. When the modified target probes are amplified as described above, the products are amplicons. Detection is accomplished in a variety of ways, but is preferably accomplished by immobilization of the amplicons, or modified target probes to a solid support.

Alternatively, detection is accomplished by non-array based methods such as mass spectrometry of capillary electrophoresis. In addition, the amplicons can be detected by liquid array, i.e. three-dimensional array methods such as flow cytometry.

When mass spectrometry is the detection method, the amplicons are applied to a mass spectrometer where their unique masses are detected as is known in the art.

When capillary electrophoresis is the detection method, amplicons are applied to a capillary electrophoresis device, and the amplicons are characterized by their electrophoretic mobility. The DNA in the capillary electrophoresis device could be detected electrically at one or more locations along the electrophoresis channel. Preferably, however, the DNA is detected optically.

When flow cytometry is the detection method, amplicons are immobilized to a support such as a microsphere as described herein. The microspheres are applied to a flow cytometer and the amplicons are detected optically as described herein.

Accordingly, upon completion of the detection or amplification reactions, target probes or readout probes as described herein become modified target probes or readout probes. Thus, modified target or readout probes can be either directly detected or subject to pre-amplification and/or amplification as described herein. The product of the pre-amplification reaction is a pre-amplification product. The product of the amplification reaction is an amplicon. While the discussion below is applicable to detection of both reaction products, i.e. modified target probes or amplicons, the terminology will be directed to detection of amplicons. Accordingly, for detection of amplicons, the present invention provides array compositions comprising array substrates with surfaces comprising discrete sites. The present invention provides methods and compositions useful in the detection of nucleic acids, particularly the labeled amplicons outlined herein. As is more fully outlined below, preferred systems of the invention work as follows. Amplicons are attached (via hybridization) to an array site. This attachment can be either directly to a capture probe on the array surface, through the use of adapters, or indirectly, using capture extender probes as outlined herein. In some embodiments, the amplicon itself comprises the labels. Alternatively, a label probe is then added, forming a detection complex. By "detection complex" is meant an amplicon hybridized with a label probe for detection. The attachment of the label probe may be direct (i.e. hybridization to a portion of the amplicon), or indirect (i.e. hybridization to an amplifier probe that hybridizes to the amplicon), with all the required nucleic acids forming an assay complex.

Accordingly, the present invention also contemplates the use of array compositions comprising at least a first array substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. A preferred embodiment utilizes microspheres on a variety of array substrates including fiber optic bundles, as are outlined in PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference. While much of the discussion below is directed to the use of microsphere arrays on fiber optic bundles, any array format of nucleic acids on solid supports may be utilized.

Arrays containing from about 2 different bioactive agents (e.g. different beads, when beads are used) to many millions can be made, with very large arrays being possible. Generally, the array will comprise from two to as many as a billion or more, depending on the size of the beads and the array substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple array substrates may be used, either of different or identical compositions. Thus for example, large arrays may comprise a plurality of smaller array substrates.

In addition, one advantage of the present compositions is that particularly through the use of fiber optic technology, extremely high density arrays can be made. Thus for example, because beads of 200 µm or less (with beads of 200 nm possible) can be used, and very small fibers are known, it is possible to have as many as 40,000 or more (in some instances, 1 million) different elements (e.g. fibers and beads) in a 1 mm² fiber optic bundle, with densities of greater than 25,000,000 individual beads and fibers (again, in some instances as many as 50–100 million) per 0.5 cm² obtainable (4 million per square cm for 5µ center-to-center and 100 million per square cm for 1µ center-to-center).

By "array substrate" or "array solid support" or other grammatical equivalents herein is meant any material that can be modified to contain discrete individual sites appropriate for the attachment or association of beads and is amenable to at least one detection method. As will be appreciated by those in the art, the number of possible array substrates is very large. Possible array substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the array substrates allow optical detection and do not themselves appreciably fluoresce.

Generally the array substrate is flat (planar), although as will be appreciated by those in the art, other configurations of array substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred array substrates include optical fiber bundles as discussed below, and flat planar array substrates such as paper, glass, polystyrene and other plastics and acrylics.

In a preferred embodiment, the array substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the arrayed array compositions of the invention can be configured in several ways; see for example U.S. Ser. No. 09/473,904, hereby expressly incorporated by reference. In a preferred embodiment, as is more fully outlined below, a "one component" system is used. That is, a first array substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

Alternatively, a "two component" system can be used. In this embodiment, the individual arrays are formed on a second array substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different array surfaces, resulting in substantially similar but perhaps not identical arrays.

At least one surface of the array substrate is modified to contain discrete, individual sites for later association of microspheres. These sites may comprise physically altered sites, i.e. physical configurations such as wells or small depressions in the array substrate that can retain the beads, such that a microsphere can rest in the well, or the use of other forces (magnetic or compressive) or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the array substrate. However, it should be noted that these sites may not be discrete sites. That is, it is possible to use a uniform surface of adhesive or chemical functionalities, for example, that allows the attachment of beads at any position. That is, the surface of the array substrate is modified to allow attachment of the microspheres at individual sites, whether or not those sites are contiguous or non-contiguous with other sites. Thus, the surface of the array substrate may be modified such that discrete sites are formed that can only have a single associated bead, or alternatively, the surface of the array substrate is modified and beads may go down anywhere, but they end up at discrete sites. That is, while beads need not occupy each site on the array, no more than one bead occupies each site.

In a preferred embodiment, the surface of the array substrate is modified to contain wells, i.e. depressions in the surface of the array substrate. This may be done as is generally known in the art using a variety of techniques, including, but not limited to, photolithography, stamping techniques, molding techniques and microetching techniques. As will be appreciated by those in the art, the technique used will depend on the composition and shape of the array substrate.

In a preferred embodiment, physical alterations are made in a surface of the array substrate to produce the sites. In a preferred embodiment, the array substrate is a fiber optic bundle and the surface of the array substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the array substrate is modified to contain chemically modified sites, that can be used to attach, either covalently or non-covalently, the microspheres of the invention to the discrete sites or locations on the array substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with an array substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. *"Microsphere Detection Guide"* from Bangs Laboratories, Fishers Ind. is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of an array substrate/bead pairing that allows the association or attachment of the beads at discrete sites on the surface of the array substrate, such that the beads do not move during the course of the assay.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidincoated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach nucleic acids to beads.

Alternatively, chemical crosslinking may be done, for example by photoactivated crosslinking of thymidine to reactive groups, as is known in the art.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads are removed.

In a preferred embodiment, when non-covalent methods are used to associate the beads with the array, a novel method of loading the beads onto the array is used. This method comprises exposing the array to a solution of particles (including microspheres and cells) and then applying energy, e.g. agitating or vibrating the mixture. In a preferred embodiment when the array substrate is a fiber optic bundle, the array substrate is tapped into the beads. That is, the energy is tapping. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

EXAMPLES

Example 1

Solid Phase Genomic DNA is Reusable

Protocol: Begin with 1 ug gDNA on 50 ug of beads. (Homozygous 1958 and 2180).
1. Hybridize OLA oligos for locus 1958. Ligate. Elute products with NaOH. Amplify by PCR.
2. Hybridize OLA oligos for locus 2180. Ligate. Elute products with NaOH. Amplify by PCR.
3. Repeat steps 1 and 2 through 6 cycles.

Analyze by agarose gel electrophoresis. See FIG. 5.

Conclusion: Genomic DNA immobilized on a solid phase is reusable at least six times. Ligase allele selectivity is quite good.

Example 2

Genomic DNA on Magnetic Particles is Reusable in the Oligonucleotide Ligation Assay Protocol: To beaded DNA-hybridize 48 SNP oligos, wash, ligate, elute, PCR amplify.

Store overnight. Mix controls. Hybridize 48 SNP oligos, wash, ligate, elute, PCR amplify.

Analyze by agarose gel electrophoresis. See FIGS. 6A and B.

What is claimed is:

1. A method comprising:
   a) providing a composition camprising first primers and at least 10 different target nucleic acids, wherein either said first primers or said at least 10 different target nucleic acids are immobilized to at least one solid support;
   b) performing a first analysis of said at least 10 different target nucleic acids, said first analysis comprising:
      i) contacting said first primers with said at least 10 different target nucleic acids whereby at least one of said first primers hybridizes with said at least 10 different target nucleic acids;
      ii) removing unhybridized first primers; and
      iii) contacting said hybridized first primers with an enzyme such that said hybridized first primers are modified forming first modified primers, whereby a sinnal is obtained from said first analysis and whereby said at least 10 different target nucleic acids is not consumed, and
   c) performing a second analysis of said at least 10 different target nucleic acids, comprising:
      i) contacting second primers with said at least 10 different target nucleic acids whereby at least one of said second primers hybridizes with said at least 10 different target nucleic acids;
      ii) removing unhybridized second primers; and
      iii) contacting said hybridized second primers with an enzyme such that said hybridized second primers are modified forming second modified primers, whereby a signal is obtained from said second analysis and wherein a signal obtained from said second analysis is not diminished more than 40% compared to a signal obtained from said first analysis.

2. The method according to claim 1, further comprising detecting said first and second modified primers.

3. The method according to claim 1, further comprising amplifying said first and second modified primers to form first and second amplicons.

4. The method according to claim 3, further comprising detecting said first and second amplicons.

5. The method according to claim 4, wherein said first and second amplicons comprise labels.

6. The method according to claim 5, wherein said first and second amplicons are labeled during said amplification.

7. The method according to claim 1, wherein said target nucleic acid comprises genomic DNA.

8. The method according to claim 7, wherein said genomic DNA comprises at least one copy of the genomic DNA from an organism.

9. The method according to claim 8, wherein said organism is selected from humans, mice, pigs, cows, bacteria, viruses or plants.

10. The method according to claim 1, wherein at least one of said first and second primers comprises an adapter sequence.

11. A method comprising:
    a) providing a composition comprising first primers and a target nucleic acid wherein said first primers are ligation primers;
    b) hybridizing said first ligation primers with said target nucleic acid to form first ligation complexes, whereby said first ligation primers hybridize to said target nucleic acid comprising a first target sequence;
    c) removing unhybridized ligation primers;
    d) contacting said first ligation complexes with a ligation enzyme, whereby when said first ligation primers are complementary to said first target sequence, said ligation enzyme ligates said first ligation primers generating first ligation products, whereby a signal is obtained from said first ligation products;
    e) removing said first ligation products from said target nucleic acid;
    f) hybridizing said target nucleic acid with second ligation primers to form second ligation complexes, whereby said second ligation primers hybridize to said target nucleic acid comprising a second target sequence, and
    g) contacting said second ligation complex with a ligation enzyme, whereby when said second ligation primers are complementary to said second target sequence, said ligation enzyme ligates said second ligation primers generating second ligation products, whereby a signal is obtained from said second ligation products and wherein a signal obtained from said second ligation products is not diminished more than 40% compared to a signal obtained from said first ligation products.

12. The method according to claim 11, further comprising:
    h) contacting said first and second ligation products with amplification primers, nucleotides and an amplification enzyme to form first and second amplicons; and
    i) detecting said first and second amplicons.

13. The method according to claim 12, wherein said amplification enzyme is a DNA polymerase and said nucleotides are dNTPs.

14. The method according to claim 12, wherein said amplification enzyme is an RNA polymerase and said nucleotides are NTPs.

15. The method according to claim 11 further comprising amplifying said first and second ligation products to form first and second amplicons.

16. The method according to claim 15, further comprising detecting said first and second amplicons.

17. The method according to claim 16, wherein said first and second amplicons comprise labels.

18. The method according to claim 17, wherein said first and second amplicons are labeled during said amplification.

19. The method according to claim 11, wherein said target nucleic acid comprises genomic DNA.

20. The method according to claim 19, wherein said genomic DNA comprises at least one copy of the genomic DNA from an organism.

21. The method according to claim 20, wherein said organism is selected from humans, mice, pigs, cows, bacteria, viruses or plants.

22. A method of reusing a target nucleic acid comprising:
a) providing a composition comprising first primers and a target nucleic acid, wherein either said first primers or said target nucleic acid are immobilized on at least one solid support;
b) performing a first analysis of said target nucleic acid, said first analysis comprising:
  i) contacting said first primers with said target nucleic acid whereby at least one of said first primers hybridizes with said target nucleic acid;
  ii) removing unhybridized first primers; and
  iii) contacting said hybridized first primers with an enzyme such that said hybridized first primers are modified forming first modified primers, whereby a signal is obtained from said first analysis and whereby said target nucleic acid is not consumed; and
c) reusing said target nucleic acid in a second analysis, whereby a signal is obtained from said second analysis and wherein a signal obtained from said second analysis is not diminished more than 40% compared to a signal obtained from said first analysis.

23. The method according to claim 22, wherein said target nucleic acid is reused at least five times.

24. The method according to claim 11 or 22, wherein said target nucleic acid is genomic DNA.

25. The method according to claim 1, 11 or 22, wherein said target nucleic acid is immobilized on at least one solid support.

26. The method according to claim 1, 11 or 22, wherein said first primers are immobilized on at least one solid support.

27. The method according to claim 1, 11 or 22, wherein at least 10 different target nucleic acids are analyzed in a single reaction.

28. The method according to claim 11 or 22, wherein at least 50 different target nucleic acids are analyzed in a single reaction.

29. The method according to claim 1, 11 or 22, wherein at least 100 different target nucleic acids are analyzed in a single reaction.

30. The method according to claim 22, further comprising amplifying said first modified primers to form first amplicons.

31. The method according to claim 30, further comprising detecting said first amplicons.

32. The method according to claim 31, wherein said first amplicons comprise labels.

33. The method according to claim 32, wherein said first amplicons are labeled during said amplification.

34. The method according to claim 32, wherein said target nucleic acid comprises genomic DNA.

35. The method according to claim 34, wherein said genomic DNA comprises at least one copy of the genomic DNA from an organism.

36. The method according to claim 35, wherein said organism is selected from humans, mice, pigs, cows, bacteria, viruses or plants.

* * * * *

UNITED STATES PATENT AND TRADEMARK OFFICE
CERTIFICATE OF CORRECTION

PATENT NO.   : 6,913,884 B2
DATED        : July 5, 2005
INVENTOR(S)  : Chee, Mark S. et al.

It is certified that error appears in the above-identified patent and that said Letters Patent is hereby corrected as shown below:

Column 41,
Line 31, please delete "camprising" and replace therefore with -- comprising --.
Line 46, please delete "sinnal" and replace therefore with -- signal --.

Column 44,
Line 7, please delete "to claim 1, 11 or 22," and replace therefore with -- to claim 11 or 22, --.
Line 12, please delete "to claim 11 or 22" and replace therefore with -- to claim 1, 11 or 22, --.
Line 26, please delete "to claim 32" and replace therefore with -- to claim 22 --.

Signed and Sealed this

Twenty-seventh Day of September, 2005

JON W. DUDAS
*Director of the United States Patent and Trademark Office*